(12) United States Patent
Ducatelle et al.

(10) Patent No.: US 7,780,951 B2
(45) Date of Patent: Aug. 24, 2010

(54) VACCINES FOR IMMUNIZATION AGAINST HELICOBACTER

(75) Inventors: Richard Ducatelle, Wortegem-Petegem (BE); Ann Hellemans, Wachtebeke (BE)

(73) Assignee: Universiteit Gent, Gent (BE)

( * ) Notice: Subject to any disclaimer, the term of this patent is extended or adjusted under 35 U.S.C. 154(b) by 290 days.

(21) Appl. No.: 11/453,170

(22) Filed: Jun. 14, 2006

(65) Prior Publication Data

US 2006/0292179 A1    Dec. 28, 2006

Related U.S. Application Data

(60) Provisional application No. 60/691,394, filed on Jun. 16, 2005, provisional application No. 60/695,995, filed on Jul. 1, 2005.

(51) Int. Cl.
  *A61K 49/00* (2006.01)
  *A61K 39/38* (2006.01)
  *A61K 47/00* (2006.01)

(52) U.S. Cl. .................. 424/9.2; 424/9.1; 424/184.1; 424/234.1; 424/278.1; 424/282.1; 536/23.1; 536/23.7

(58) Field of Classification Search .............. 424/9.1, 424/9.2, 184.1, 234.1, 278.1, 282.1; 536/23.1, 536/23.7

See application file for complete search history.

(56) References Cited

U.S. PATENT DOCUMENTS 5,538,729 A * 7/1996 Czinn et al. ............... 424/234.1
5,843,460 A * 12/1998 Labigne et al. ........... 424/234.1

FOREIGN PATENT DOCUMENTS

| WO | WO94/26901 | 11/1994 |
| WO | WO2004/069184 | 8/2004 |
| WO | PCT/EP2006/005616 | 12/2006 |
| WO | WO 2006/133879 | 12/2006 |

OTHER PUBLICATIONS

Park, J.-H., et al. "Experimental Infection of mice with tightly coiled spiral bacteria ("*Candidatus Helico bacter suis*") originating from the pig stomach". J. Comp. Path., vol. 129, pp. 154-160, 2003.*
Jalava, K., et al. A cultured strain of "*Helicobacter heilmannii*," a human gastric pathogen, identified as *H. bizzozeronii*: Evidence for zoonotic potential of *Helicobacter*. Emerging Infectious Diseases, 2001, vol. 7, No. 6, pp. 1-36-1038.*

Hanninen, M.-L., et al. culture and characteristics of *Helicobacter bizzozeronii*, a new canine gastric *Helicobacter* sp. International Journal of Systematic Bacteriology, 1996, vol. 46, No. 1, pp. 160-166.*
Aebischer et al., "Development of a Vaccine Against '*Helicobacter pylori*'," Abstracts of the XVIIIth International Workshop on Gastrointestinal Pathology and *Helicobacter*. European *Helicobacter* Study Group, Copenhagen, Oct. 12-14, 2005. *Helicobacter* 10:485-556, Abstract No. 14.09.
De Groote et al., "Detection of '*Candidatus Helicobacter suis*' in gastric samples of pigs by PCR: comparison with other invasive diagnostic techniques," J Clin Microbiol. 38:1131-5 (2000).
Dieterich et al., "Urease-based mucosal immunization against '*Helicobacter heilmannil*' Infection Induces corpus atrophy in mice," Infect Immun. 67:6206-9 (1999).
Hellemans et al., "Protective Immunization against '*Candidatus Helicobacter suis*' with heterologous antigens of *H. pylori* and *H. felis*," Vaccine. 24:2469-76 (2006).
Communication Relating to the Results of the Partial International Search (PCT/EP2006/005616).
Hellemans et al., "Protective Immunization Against "*Candidatus Helicobacter suis*" with Heterologous Antigens Stimulates Long-Term Immunity," Abstracts of the XVIIIth International Workshop on Gastrointestinal Pathology and Heliobacter. European *Helicobacter* Study Group. Copenhagen, Oct. 12-14, 2005, *Helicobacter* 10:458-556, Abstract No. 14.08.
International Search Report issued on PCT/EP2008/005618 (Mailed Feb. 13, 2007).
Written Opinion focused on PCT/EP2006/005616 (Mailed Feb. 13, 2007).
Jalava et al., "Isolation and Identification of *Helicobacter* spp. from Canine and Feline Gastric Mucosa," Appl. Environ. Microbiol. 64(10):3998-4006 (1998).
GenBank Accession No. AF127028, submitted Nov. 17, 1999.
Evans et al., "Genetic Evidence for Host Specificity in the Adhesin-Encoding Genes *hxaA* of *Helicobacter acinonyx*, *hnaA* of *H. nemestrinae* and *hpaA* of *H. pylori*," Gene 163(1):97-102 (1995).
Suerbaum et al, "*Helicobacter nemestrinae* ATCC 49396$^T$ is a Strain of *Helicobacter pylori* (Marshall et al. 1985) Goodwin et al. 1989, and *Helicobacter nemestrinae* Bronsdon et al. 1991 Is Therefore a Junior Heterotypic Synonym of *Helicobacter pylori*," Int. J. Syst. Evol. Microbiol. 52(pt. 2):437-439 (2002).
Office Action for U.S. Appl. No. 12/044,533, issued Sep. 29, 2008.
Office Action for U.S. Appl. No. 12/044,533, issued Apr. 13, 2009.
International Preliminary Report on Patentability for International Application PCT/EP2006/005616, dated Dec. 17, 2007.
Office Action for U.S. Appl. No. 12/044,533, issued Dec. 3, 2009.

* cited by examiner

*Primary Examiner*—Rodney P. Swartz
(74) *Attorney, Agent, or Firm*—Clark & Elbing LLP

(57) ABSTRACT

The invention relates to the immunization of pigs against Candidatus *Helicobacter suis* using antigens of species related to Candidatus *Helicobacter suis*.

21 Claims, 9 Drawing Sheets

Figure 1:
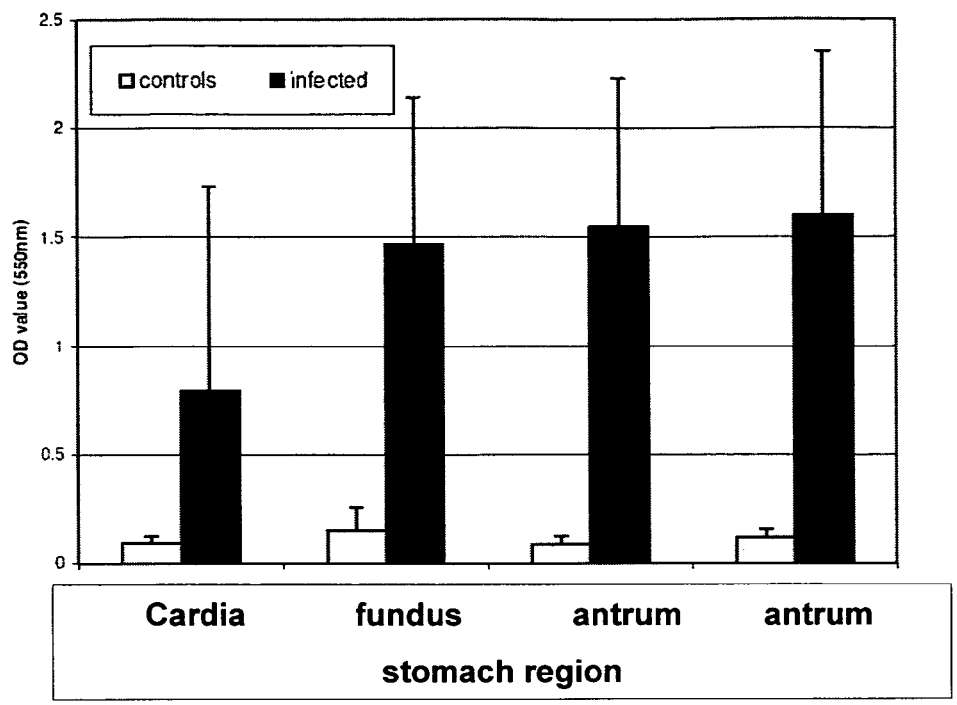

| | H. aurati MIT 97-5075c (AF297868) | H. pametensis (AF302105) | H. cholecystus Hkb-1 (U46129) | H. pullorum (AJ876518) | H. fennelliae CCUG 18820 (M88154) | H. mesocricetorum (AF072334) | H. rodentium (U96297) | H. ganmani (AY631951) | H. canadensis NLEP-16143 (AF262037) | "Candidatus H. bovis" (AF127027) | H. pylori (AF302106) | H. nemestrinae (AF363064) | H. acinonychis Eaton 90-119-3 (M88148) | H. bizzozeronii CCUG 35046 (AF302107) |
|---|---|---|---|---|---|---|---|---|---|---|---|---|---|---|
| H. aurati MIT 97-5075c (AF297868) | 0 | 3.08 | 4.03 | 4.10 | 5.86 | 3.86 | 4.75 | 4.84 | 3.48 | 9.69 | 6.83 | 6.69 | 7.18 | 8.07 |
| H. pametensis (AF302105) | 3.08 | 0 | 1.83 | 3.03 | 6.90 | 3.80 | 4.24 | 4.38 | 2.78 | 8.15 | 6.02 | 5.83 | 6.52 | 6.64 |
| H. cholecystus Hkb-1 (U46129) | 4.03 | 1.83 | 0 | 3.99 | 7.37 | 5.33 | 4.50 | 5.30 | 3.22 | 8.63 | 6.89 | 6.56 | 7.06 | 6.73 |
| H. pullorum (AJ876518) | 4.10 | 3.03 | 3.99 | 0 | 5.30 | 4.12 | 4.44 | 4.34 | 2.23 | 8.87 | 5.85 | 5.76 | 6.39 | 6.74 |
| H. fennelliae CCUG 18820 (M88154) | 5.84 | 6.90 | 7.37 | 5.30 | 0 | 7.06 | 7.37 | 6.89 | 6.90 | 11.61 | 9.99 | 9.89 | 10.48 | 10.05 |
| H. mesocricetorum (AF072334) | 3.86 | 3.80 | 5.33 | 4.12 | 7.06 | 0 | 2.95 | 3.19 | 4.01 | 9.93 | 6.24 | 6.55 | 7.34 | 8.51 |
| H. rodentium (U96297) | 4.75 | 4.24 | 4.50 | 4.44 | 7.37 | 2.95 | 0 | 2.08 | 3.25 | 9.09 | 6.54 | 6.69 | 7.51 | 7.85 |
| H. ganmani (AY631951) | 4.84 | 4.38 | 5.30 | 4.34 | 6.89 | 3.19 | 2.08 | 0 | 3.96 | 9.95 | 6.87 | 7.14 | 7.92 | 7.71 |
| H. canadensis NLEP-16143 (AF262037) | 3.48 | 2.78 | 3.22 | 2.23 | 6.90 | 4.01 | 3.25 | 3.96 | 0 | 8.32 | 5.97 | 5.92 | 6.34 | 6.73 |
| "Candidatus H. bovis" (AF127027) | 9.69 | 8.15 | 8.63 | 8.87 | 11.61 | 9.93 | 9.09 | 9.95 | 8.32 | 0 | 10.72 | 10.64 | 11.21 | 10.89 |
| H. pylori (AF302106) | 6.83 | 6.02 | 6.89 | 5.85 | 9.99 | 6.24 | 6.54 | 6.87 | 5.97 | 10.72 | 0 | 0.49 | 2.54 | 5.26 |
| H. nemestrinae (AF363064) | 6.69 | 5.83 | 6.56 | 5.76 | 9.89 | 6.55 | 6.69 | 7.14 | 5.92 | 10.64 | 0.49 | 0 | 2.19 | 5.36 |
| H. acinonychis Eaton 90-119-3 (M88148) | 7.18 | 6.52 | 7.06 | 6.39 | 10.48 | 7.34 | 7.51 | 7.92 | 6.34 | 11.21 | 2.54 | 2.19 | 0 | 4.92 |
| H. bizzozeronii CCUG 35046 (AF302107) | 8.07 | 6.64 | 6.73 | 6.74 | 10.05 | 8.51 | 7.85 | 7.71 | 6.73 | 10.89 | 5.26 | 5.36 | 4.92 | 0 |
| "Candidatus H. heilmannii" BC1 (AF506772) | 8.50 | 7.42 | 7.36 | 7.01 | 10.10 | 8.81 | 8.38 | 7.99 | 7.05 | 11.26 | 5.36 | 5.32 | 4.51 | 1.90 |
| H. felis ATCC 49179 (M57398) | 7.96 | 6.80 | 6.85 | 6.60 | 9.98 | 8.89 | 8.07 | 7.77 | 6.73 | 10.00 | 4.73 | 4.76 | 4.19 | 1.19 |
| H. salomonis Inkinen (U89351) | 8.36 | 6.74 | 6.78 | 6.79 | 10.25 | 8.88 | 8.29 | 8.14 | 7.26 | 11.07 | 4.96 | 4.89 | 4.38 | 1.11 |
| H. cynogastricus JKM4 (DQ004689) | 8.57 | 7.35 | 7.22 | 7.00 | 10.12 | 9.03 | 8.68 | 8.54 | 7.56 | 11.59 | 5.35 | 5.28 | 4.60 | 1.62 |
| "Candidatus H. suis" (AF127028) | 9.11 | 7.95 | 8.72 | 7.56 | 10.33 | 8.60 | 8.49 | 7.77 | 7.55 | 11.27 | 6.06 | 6.16 | 6.38 | 3.55 |
| H. trogontum (AY686609) | 3.95 | 3.80 | 4.40 | 3.86 | 5.68 | 4.53 | 4.60 | 4.79 | 4.39 | 9.00 | 7.50 | 7.62 | 7.74 | 7.66 |
| H. typhlonius (AF061104) | 4.25 | 4.83 | 4.54 | 4.91 | 6.84 | 6.16 | 5.50 | 6.78 | 4.00 | 9.63 | 8.07 | 7.81 | 8.33 | 7.98 |
| H. muridarum (M80205.2) | 3.95 | 4.16 | 3.87 | 5.05 | 6.64 | 5.82 | 5.27 | 5.88 | 3.52 | 9.17 | 7.33 | 7.61 | 7.89 | 7.56 |
| H. mustelae (M35310) | 5.58 | 3.38 | 4.36 | 6.17 | 13.67 | 5.47 | 3.60 | 7.60 | 3.92 | 7.62 | 7.89 | 7.60 | 7.31 | 7.58 |
| H. hepaticus (U07575) | 16.62 | 16.83 | 17.05 | 17.68 | 19.21 | 18.18 | 17.48 | 18.16 | 15.77 | 20.90 | 19.51 | 19.37 | 19.88 | 19.85 |
| H. canis (L13464) | 4.45 | 3.82 | 3.68 | 4.43 | 6.92 | 5.39 | 4.70 | 5.83 | 3.43 | 9.27 | 6.72 | 6.71 | 7.48 | 7.67 |
| H. cinaedi (AF497810) | 4.53 | 3.79 | 3.74 | 5.02 | 7.20 | 5.30 | 4.46 | 5.45 | 3.40 | 8.99 | 7.70 | 7.44 | 8.01 | 8.09 |
| H. bilis (U18766) | 4.19 | 3.35 | 3.29 | 4.48 | 6.73 | 5.04 | 4.14 | 5.22 | 3.34 | 8.71 | 7.08 | 6.76 | 7.86 | 8.01 |
| Wolinella succinogenes (M88159) | 7.40 | 6.95 | 7.19 | 7.81 | 9.81 | 8.93 | 7.66 | 9.28 | 7.63 | 12.48 | 10.62 | 10.36 | 10.79 | 11.06 |

Figure 9b

| | "Candidatus H. heilmannii" BC1 (AF506772) | H. felis ATCC 49179 (M57398) | H. salomonis Inkinen (U89351) | H. cynogastricus JKM4 (DQ004689) | "Candidatus H. suis" (AF127028) | H. trogontum (AY686609) | H. typhlonius (AF061104) | H. muridarum (M80205.2) | H. muscelae (M55310) | H. hepaticus (U07575) | H. canis (L13464) | H. cinaedi (AF498710) | H. bilis (U18766) | Wolinella succinogenes 29543 (M88159) |
|---|---|---|---|---|---|---|---|---|---|---|---|---|---|---|
| H. aurati MIT 97-5075c (AF297868) | 8.50 | 7.96 | 8.36 | 8.57 | 9.11 | 3.95 | 4.25 | 3.95 | 5.38 | 16.62 | 4.45 | 4.53 | 4.19 | 7.40 |
| H. pametensis (AF302105) | 7.42 | 6.80 | 6.74 | 7.35 | 7.95 | 3.80 | 4.83 | 4.16 | 3.38 | 16.83 | 3.82 | 3.79 | 3.35 | 6.95 |
| H. cholecystus Hkb-1 (U46129) | 7.36 | 6.85 | 6.78 | 7.22 | 8.72 | 4.40 | 4.54 | 3.87 | 4.36 | 17.05 | 3.68 | 3.74 | 3.29 | 7.19 |
| H. pullorum (AJ876518) | 7.01 | 6.60 | 6.79 | 7.00 | 7.56 | 3.86 | 4.91 | 5.05 | 6.17 | 17.68 | 4.43 | 5.02 | 4.48 | 7.82 |
| H. fennelliae CCUG 18820 (M88154) | 10.10 | 9.98 | 10.25 | 10.12 | 10.33 | 5.68 | 6.84 | 6.64 | 13.67 | 19.21 | 6.92 | 7.20 | 6.73 | 9.81 |
| H. mesocricetorum (AF072334) | 8.81 | 8.89 | 8.88 | 9.03 | 8.60 | 4.53 | 6.16 | 5.82 | 5.47 | 18.18 | 5.39 | 5.30 | 5.04 | 8.93 |
| H. rodentium (U96297) | 8.38 | 8.07 | 8.29 | 8.68 | 8.49 | 4.60 | 5.50 | 5.27 | 3.60 | 17.48 | 4.70 | 4.46 | 4.14 | 7.66 |
| H. ganmani (AY631951) | 7.99 | 7.77 | 8.14 | 8.54 | 7.77 | 4.79 | 6.78 | 5.88 | 7.60 | 18.16 | 5.83 | 5.45 | 5.22 | 9.28 |
| H. canadensis NLEP-16143 (AF262037) | 7.05 | 6.73 | 7.26 | 7.56 | 7.55 | 4.39 | 4.00 | 3.52 | 3.92 | 15.77 | 3.43 | 3.40 | 3.34 | 7.63 |
| "Candidatus H. bovis" (AF127027) | 11.26 | 11.00 | 11.07 | 11.59 | 11.27 | 9.00 | 9.63 | 9.17 | 7.62 | 20.90 | 9.27 | 8.99 | 8.71 | 12.48 |
| H. pylori (AF302106) | 5.36 | 4.73 | 4.96 | 5.35 | 6.06 | 7.50 | 8.07 | 7.33 | 7.89 | 19.51 | 6.72 | 7.70 | 7.08 | 10.62 |
| H. nemestrinae (AF363064) | 5.32 | 4.76 | 4.89 | 5.28 | 6.16 | 7.62 | 7.81 | 7.61 | 7.60 | 19.37 | 6.71 | 7.44 | 6.76 | 10.36 |
| H. acinonychis Eaton 90-119-3 (M88148) | 4.51 | 4.19 | 4.38 | 4.60 | 6.38 | 7.74 | 8.33 | 7.89 | 7.31 | 19.88 | 7.48 | 8.01 | 7.86 | 10.79 |
| H. bizzozeronii CCUG 35046 (AF302107) | 1.90 | 1.19 | 1.11 | 1.62 | 3.55 | 7.66 | 7.98 | 7.56 | 7.58 | 19.85 | 7.67 | 8.09 | 8.01 | 11.06 |
| "Candidatus H. heilmannii" BC1 (AF506772) | 0 | 1.38 | 1.42 | 1.59 | 3.74 | 8.16 | 8.65 | 8.25 | 9.03 | 20.68 | 8.00 | 8.57 | 8.45 | 11.60 |
| H. felis ATCC 49179 (M57398) | 1.38 | 0 | 0.75 | 1.04 | 4.22 | 7.57 | 8.34 | 7.93 | 8.78 | 20.19 | 7.65 | 8.37 | 8.06 | 11.37 |
| H. salomonis Inkinen (U89351) | 1.42 | 0.75 | 0 | 0.68 | 3.92 | 7.89 | 8.50 | 8.26 | 8.49 | 20.30 | 7.71 | 8.60 | 8.29 | 11.73 |
| H. cynogastricus JKM4 (DQ004689) | 1.59 | 1.04 | 0.68 | 0 | 4.23 | 8.03 | 8.76 | 8.47 | 9.32 | 20.63 | 7.71 | 8.98 | 8.51 | 11.92 |
| "Candidatus H. suis" (AF127028) | 3.74 | 4.22 | 3.92 | 4.23 | 0 | 8.67 | 8.83 | 8.81 | 9.00 | 20.69 | 8.40 | 8.50 | 8.65 | 12.40 |
| H. trogontum (AY686609) | 8.16 | 7.57 | 7.89 | 8.03 | 8.67 | 0 | 3.84 | 3.77 | 3.38 | 16.53 | 3.77 | 3.84 | 3.60 | 7.16 |
| H. typhlonius (AF061104) | 8.65 | 8.34 | 8.50 | 8.76 | 8.83 | 3.84 | 0 | 2.54 | 3.85 | 17.17 | 2.71 | 2.94 | 6.60 | 7.77 |
| H. muridarum (M80205.2) | 8.25 | 7.93 | 8.26 | 8.47 | 8.80 | 3.77 | 2.54 | 0 | 3.38 | 15.73 | 3.54 | 3.69 | 3.37 | 7.37 |
| H. muscelae (M55310) | 9.08 | 8.78 | 8.49 | 9.32 | 9.00 | 3.38 | 3.85 | 3.38 | 0 | 3.47 | 3.52 | 2.84 | 2.79 | 5.26 |
| H. hepaticus (U07575) | 20.68 | 20.19 | 20.30 | 20.63 | 20.69 | 16.53 | 17.17 | 15.73 | 3.47 | 0 | 16.05 | 15.57 | 15.43 | 21.08 |
| H. canis (L13464) | 8.00 | 7.65 | 7.71 | 7.71 | 8.40 | 3.77 | 2.71 | 3.54 | 3.52 | 16.05 | 0 | 1.93 | 1.33 | 7.76 |
| H. cinaedi (AF498710) | 8.57 | 8.37 | 8.60 | 8.98 | 8.50 | 3.84 | 2.94 | 3.69 | 2.84 | 15.57 | 1.93 | 0 | 1.01 | 7.51 |
| H. bilis (U18766) | 8.45 | 8.06 | 8.29 | 8.51 | 8.65 | 3.60 | 6.60 | 3.37 | 2.79 | 15.43 | 1.33 | 1.01 | 0 | 7.41 |
| Wolinella succinogenes (M88159) | 11.60 | 11.37 | 11.73 | 11.92 | 12.40 | 7.16 | 7.77 | 7.37 | 5.23 | 21.08 | 7.76 | 7.51 | 7.41 | 0 |

Figure 9b (continued)

```
tagtttgatc ctggctcaga gtgaacgctg gcggcgtgcc taatacatgc aagtcgaacg    60
atgaagccta gcttgctagg tggattagtg gcgcacgggt gagtaacgca tagatgacat   120
gcccttagt  ttgggatagc cactagaaat ggtgattaat accaaatact accctatggg   180
ggaaagattt atcgctaaag gattggtcta tgtcctatca gcttgttggt gaggtaaagg   240
ctcaccaagg caatgacggg tatccggcct gagagggtga acggacacac tggaactgag   300
acacggtcca gactcctacg ggaggcagca gtagggaata ttgctcaatg ggcgcaagcc   360
tgaagcagca acgccgcgtg gaggatgaag gttttaggga ttgtaaactt cctttttgtca  420
gagaagatta atgacggtat ctgacgaata agcaccggct aactccgtgc cagcagccgc   480
ggtaatacgg agggtgcaag cgttactcgg aatcactggg cgtaaagagt gcgtaggcgg   540
ggttgtaagt cagatgtgaa atcctatggc ttaaccatag aactgcattt gaaactacaa   600
ctctggagtg tgggagaggt aggtggaatt cttggtgtag gggtaaaatc cgtagagatc   660
aagaggaata ctcattgcga aggcgacctg ctggaacaat actgacgctg attgcacgaa   720
agcgtgggga gcaaacagga ttagataccc tggtagtcca cgccctaaac gatggatgct   780
agttgttggg gggctttgtc ctcccagtaa tgcagctaac gccttaagca tcccgcctgg   840
ggagtacggt cgcaagatta aaactcaaag gaatagacgg ggaccgcac aagcggtgga    900
gcatgtggtt taaattcgaa gatacacgaa gaaccttacc taggcttgac attgaaggaa   960
tttgctagaa atagcgaagt gtctagcttg ctagaccctg aaaacaggtg ctgcacggct  1020
gtcgtcagct cgtgtcgtga gatgttgggt taagtcccgc aacgagcgca accctctttc  1080
ttagttgcta acagatcatg ctgagctctc taagaatact gcctgcgtaa gcaggaggaa  1140
ggtgaggacg acgtcaagtc atcatggccc ttacgcctag gctacacac gtgctacaat   1200
ggggtgcaca aagagatgca atgccgcgag gctgagccaa tcttaaaaac gcctctcagt  1260
tcggattgca ggctgcaact cgcctgcatg aagctggaat cgctagtaat cgcaaatcag  1320
ccatgttgcg gtgaatacgt tcccgggtct tgtactcacc gcccgtcaca ccatgggagt  1380
tgtgtttgcc ttaagtcagg atgctaaagt agctactgcc cacggcacac acagcgactg  1440
ggacgaagtc gtaacaaggt aa                                            1462
```
[SEQ ID NO:5]

Figure 11

SEQUENCE LISTING

<160> NUMBER OF SEQ ID NOS: 15

<210> SEQ ID NO 1
<211> LENGTH: 22
<212> TYPE: DNA
<213> ORGANISM: artificial
<220> FEATURE:
<223> OTHER INFORMATION: PCR Primer HS 586 for 16S rRNA gene of
      Candidatus Helicobacter suis

<400> SEQUENCE: 1
gggaggacaa gtcaggtgtg aa                                             22

<210> SEQ ID NO 2
<211> LENGTH: 23
<212> TYPE: DNA
<213> ORGANISM: artificial
<220> FEATURE:
<223> OTHER INFORMATION: PCR primer HS641 for 16S rRNA gene from
      Candidatus Helicobacter suis

<400> SEQUENCE: 2
tctcccacac tccagaagga tag                                            23

<210> SEQ ID NO 3
<211> LENGTH: 18
<212> TYPE: DNA
<213> ORGANISM: artificial
<220> FEATURE:
<223> OTHER INFORMATION: PCR consensus primer 16S rRNA alpha/beta-NOT

<400> SEQUENCE: 3
tcaaactagg accgagtc                                                  18

<210> SEQ ID NO 4
<211> LENGTH: 20
<212> TYPE: DNA
<213> ORGANISM: artificial
<220> FEATURE:
<223> OTHER INFORMATION: PCR consensus primer 16S rRNA omega-MB

<400> SEQUENCE: 4
taccttgtta cttcacccca                                                20

<210> SEQ ID NO 5
<211> LENGTH: 1462
<212> TYPE: DNA
<213> ORGANISM: Helicobacter cynogastricus

<400> SEQUENCE: 5
tagtttgatc ctggctcaga gtgaacgctg gcggcgtgcc taatacatgc aagtcgaacg     60
atgaagccta gcttgctagg tggattagtg gcgcacgggt gagtaacgca tagatgacat    120 gcccttagt ttgggatagc cactagaaat ggtgattaat accaaatact accctatggg    180
ggaaagattt atcgctaaag gattggtcta tgtcctatca gcttgttggt gaggtaaagg    240
ctcaccaagg caatgacggg tatccggcct gagagggtga acggacacac tggaactgag    300
acacggtcca gactcctacg ggaggcagca gtagggaata ttgctcaatg ggcgcaagcc    360
tgaagcagca acgccgcgtg gaggatgaag gttttaggga ttgtaaactt ccttttgtca    420
gagaagatta atgacggtat ctgacgaata agcaccggct aactccgtgc cagcagccgc    480
ggtaatacgg agggtgcaag cgttactcgg aatcactggg cgtaaagagt gcgtaggcgg    540

```
ggttgtaagt cagatgtgaa atcctatggc ttaaccatag aactgcattt gaaactacaa    600
ctctggagtg tgggagaggt aggtggaatt cttggtgtag gggtaaaatc cgtagagatc    660
aagaggaata ctcattgcga aggcgacctg ctggaacaat actgacgctg attgcacgaa    720
agcgtgggga gcaaacagga ttagataccc tggtagtcca cgccctaaac gatggatgct    780
agttgttggg gggctttgtc ctcccagtaa tgcagctaac gccttaagca tcccgcctgg    840
ggagtacggt cgcaagatta aaactcaaag gaatagacgg ggacccgcac aagcggtgga    900
gcatgtggtt taaattcgaa gatacacgaa gaaccttacc taggcttgac attgaaggaa    960
tttgctagaa atagcgaagt gtctagcttg ctagaccctg aaaacaggtg ctgcacggct   1020
gtcgtcagct cgtgtcgtga gatgttgggt taagtcccgc aacgagcgca accctctttc   1080
ttagttgcta acagatcatg ctgagctctc taagaatact gcctgcgtaa gcaggaggaa   1140
ggtgaggacg acgtcaagtc atcatggccc ttacgcctag gctacacac gtgctacaat   1200 ggggtgcaca aagagatgca atgccgcgag gctgagccaa tcttaaaaac gcctctcagt   1260
tcggattgca ggctgcaact cgcctgcatg aagctggaat cgctagtaat cgcaaatcag   1320
ccatgttgcg gtgaatacgt tcccgggtct tgtactcacc gcccgtcaca ccatgggagt   1380
tgtgtttgcc ttaagtcagg atgctaaagt agctactgcc cacggcacac acagcgactg   1440
ggacgaagtc gtaacaaggt aa                                            1462

<210> SEQ ID NO 6
<211> LENGTH: 18
<212> TYPE: DNA
<213> ORGANISM: Artificial
<220> FEATURE:
<223> OTHER INFORMATION: sequence primer 16s rRNA H. cynogastricus

<400> SEQUENCE: 6
gtattaccgc ggctgctg                                                   18

<210> SEQ ID NO 7
<211> LENGTH: 20
<212> TYPE: DNA
<213> ORGANISM: Artificial
<220> FEATURE:
<223> OTHER INFORMATION: sequence primer 16S rRNA H. cynogastricus

<400> SEQUENCE: 7
ctcctacggg aggcagcagt                                                 20

<210> SEQ ID NO 8
<211> LENGTH: 20
<212> TYPE: DNA
<213> ORGANISM: Artificial
<220> FEATURE:
<223> OTHER INFORMATION: sequence primer 16S rRNA H. cynogastricus

<400> SEQUENCE: 8
gttgcgctcg ttgcgggact                                                 20

<210> SEQ ID NO 9
<211> LENGTH: 19
<212> TYPE: DNA
<213> ORGANISM: Artificial
<220> FEATURE:
<223> OTHER INFORMATION: sequence primer 16S rRNA H. cynogastricus

<400> SEQUENCE: 9
```

```
aactcaaagg aattgacgg                                                  19

<210> SEQ ID NO 10
<211> LENGTH: 19
<212> TYPE: DNA
<213> ORGANISM: Artificial
<220> FEATURE:
<223> OTHER INFORMATION: PCR primer Helicobacter urease

<400> SEQUENCE: 10
ckgawttgat gcaagaagg                                                  19

<210> SEQ ID NO 11
<211> LENGTH: 22
<212> TYPE: DNA
<213> ORGANISM: Artificial
<220> FEATURE:
<223> OTHER INFORMATION: PCR primer Helicobacter urease

<400> SEQUENCE: 11
cttcgtgrat tttaarrcca at                                              22

<210> SEQ ID NO 12
<211> LENGTH: 19
<212> TYPE: DNA
<213> ORGANISM: Artificial
<220> FEATURE:
<223> OTHER INFORMATION: tRNA intergenic length polymorphism primer

<400> SEQUENCE: 12
aggtcgcggg ttcgaatcc                                                  19

<210> SEQ ID NO 13
<211> LENGTH: 20
<212> TYPE: DNA
<213> ORGANISM: Artificial
<220> FEATURE:
<223> OTHER INFORMATION: PCR primer Helicobacter urease

<400> SEQUENCE: 13
accaactggg ctaagcgacc                                                 20

<210> SEQ ID NO 14
<211> LENGTH: 20
<212> TYPE: DNA
<213> ORGANISM: Artificial
<220> FEATURE:
<223> OTHER INFORMATION: primer Helicobacter urease gene

<400> SEQUENCE: 14
gckgawttga tgcaagaagg                                                 20

<210> SEQ ID NO 15
<211> LENGTH: 22
<212> TYPE: DNA
<213> ORGANISM: Artificial
<220> FEATURE:
<223> OTHER INFORMATION: primer Helicobacter urease gene

<400> SEQUENCE: 15
cttcgtgrat tttaarrcca at                                              22
```

VACCINES FOR IMMUNIZATION AGAINST HELICOBACTER

CROSS-REFERENCE TO RELATED APPLICATIONS

This application claims the benefit of the filing date of U.S. provisional patent application No. 60/691,394, filed Jun. 16, 2005, and U.S. provisional patent application No. 60/695,995, filed Jul. 1, 2005, the disclosures of each of which are incorporated herein by reference.

FIELD OF THE INVENTION

The present invention relates to tools and methods for the immunization of animals against infection by *Helicobacter* species.

BACKGROUND OF THE INVENTION

*Helicobacter* (*H.*) *pylori* infections in humans are a major cause of gastric and duodenal ulceration as well as gastric cancer. Triple therapies with proton pump inhibitors and clarithromycin and amoxicillin are recommended as first line treatment. These standard therapies increasingly face problems with antibiotic resistance and recurrence of infection, especially in areas where *H. pylori* is endemic. Various studies in animal models have shown the feasibility of both prophylactic and therapeutic vaccination against *H. pylori* (Del Guidice (2001) *Annu. Rev. Immunol.* 19, 523-563; Sanchez et al. (2001) *FEMS Immunol Med Microbiol.* 30, 157-165). *H. pylori* proteins expressed in infected mice and hence exposed to the mouse immune system, appear similar to those detected in human infections, suggesting that the mouse model is suitable for the preclinical screening of antigen candidates (Bumann et al. (2002) *Inf. Imm.* 70, 6494-6498). Immunizations with recombinant urease was found to induce local and serum immune responses in mice and protect against *Helicobacter pylori* infection (Kleanthous et al. (1998) *Inf. Imm.* 66, 2879-2886).

*H. pylori* is not the only bacterial pathogen capable of colonizing the human gastric mucosa. "*H. heilmannii*" indeed has been found in approximately 0.96% of gastric biopsies. This organism is strongly associated with gastritis, but also with peptic ulceration, gastric adenocarcinoma and mucosa associated lymphoid tissue (MALT) lymphoma.

Some studies revealed sufficient antigenic cross-reactivity between *H. felis* and *H. pylori* to generate protection to *H. felis* challenge following immunization with a *H. pylori* sonicated antigen solution (Lee & Chen (1994) *Inf. Imm.* 62, 3594-3597; Michettti et al. (1994) *Gastroenterology* 107, 1002-1011). One study shows that *H. heilmannii* infection can be prevented by vaccination both with *H. heilmannii* UreB and *H. pylori* UreAB, confirming that protective immunity against *Helicobacter* infections can be elicited by homologous as well as heterologous *Helicobacter* urease (Dieterich et al. (1999) *Inf. Imm.* 67, 6206-6209).

Recently it has been shown that *H. heilmannii* does not represent a single species, but a group of different bacterial species with a similar spiral morphology, most of which are probably zoonotic in origin. On the basis of 16S rRNA sequences, "*H. heilmannii*" has been classified into two types (Solnick et al. (1993) *J. Infect. Dis.* 168, 379-385). '*H. heilmannii*' type 2 organisms are closely related, if not identical, to the canine and feline *Helicobacter* spp., namely *H. felis*, *H. bizzozeronii* and *H. salomonis*. More than 50% of the "*H. heilmannii*" infections in humans however are due to "*H. heilmannii*" type 1. It is now accepted that "*H. heilmannii*" type 1 is identical to "Candidatus *H. suis*" (O'Rourke et al. (2004) *Int J Syst Evol Microbiol.* 54, 2203-2212; De Groote et al. (1999) *Int. J. Syst Bacteriol.* 49, 1769-1777), a spirally shaped bacterium that colonizes the stomach of more than 60% of slaughterpigs.

Little information is available in the literature on the potential of vaccine-induced protection against non-pylori helicobacter strains, such as "Candidatus *H. suis*".

In vitro cultivation of "Candidatus *H. suis*" currently is not possible, but mouse inoculation can be used to grow and maintain this bacterium viable for more than two years starting from infected pig stomach mucosa (Mendes et al. (1991) cited above; Dick et al. (1989) *J. Med. Microbiol.* 29, 55-62; Park et al. (2003) *J. Comp. Pathol.* 129:154-160).

SUMMARY OF THE INVENTION

The present invention relates to the use of an antigen preparation of a species related to a Candidatus *Helicobacter suis* for vaccination of animals against *Helicobacter* species, more particularly against Candidatus *H. suis*.

A first aspect of the invention thus relates to the use of a composition comprising one or more antigen preparations of one or more species related to Candidatus *H. suis* for the manufacture of a vaccine against *Helicobacter* species, more particularly against Candidatus *H. suis*. More particularly, the bacterial species related to Candidatus *Helicobacter suis* envisaged within the context of the present invention is/are species of bacteria having a 16S rRNA sequence having at least 93% sequence identity to the sequence of Candidatus *Helicobacter suis*. According to a particular embodiment the composition used comprises one or more antigen preparations of one or more species related to Candidatus *Helicobacter suis* selected from the group consisting of *Helicobacter felis*, *Helicobacter salomonis*, *Helicobacter heilmannii* (type II), *Helicobacter cynogastricus*, *Helicobacter pylori* or *Helicobacter bizzozeronii*.

According to particular embodiments of the invention the species related to Candidatus *Helicobacter suis* is/are selected from *H. felis*, *H. bizzozeronii* or *H. cynogastricus*. A further embodiment of the invention relates the use of an antigen preparation of *H. cynogastricus* in the preparation of a vaccine against *Helicobacter* species, more particularly against Candidatus *H. suis*.

A further aspect of the invention thus provides vaccines for use in the vaccination of animals against *Helicobacter* spp. (species), more particularly against Candidatus *H. suis*. More particularly, the vaccines of the present invention comprise one or more antigen preparations of one or more bacterial species related to Candidatus *Helicobacter suis* envisaged within the context of the present invention is/are species of bacteria having a 16S rRNA sequence having at least 93% sequence identity to the sequence of Candidatus *Helicobacter suis*. According to a particular embodiment the vaccines comprise one or more antigen preparations of one or more species related to Candidatus *Helicobacter suis* selected from the group consisting of *Helicobacter felis*, *Helicobacter salomonis*, *Helicobacter heilmannii* (type II), *Helicobacter cynogastricus*, *Helicobacter pylori* or *Helicobacter bizzozeronii*. The vaccines can further optionally comprise an adjuvant and/or a pharmaceutically acceptable carrier.

The vaccines of the present invention can be used for either prophylactic or therapeutic immunization and suitable vaccination routes include, but are not limited to, intranasal, subcutaneous and intramuscular immunization. Suitable vaccination routes also comprise combination administrations (e.g. oral/intramuscular administration).

According to a particular embodiment the antigen preparation used in the preparation of a vaccine comprises a lysate of bacteria. Alternative embodiments include vaccines wherein the antigen preparation comprises whole-killed bacteria or live-attenuated bacteria. Additionally or alternatively the vaccine according to the invention comprises an antigen preparation which comprises a processed and/or artificial bacterial preparation.

A further aspect of the invention relates to methods of vaccinating an animal against *Helicobacter* spp. infection, more particularly against a Candidatus *H. suis* infection comprising the step of administering a composition comprising one or more antigen preparations of one or more species related to a Candidatus *H. suis* to the animal, either before infection (for prophylactic vaccination) or after infection has been identified (as therapeutic vaccination). Optionally the antigen preparation is administered together with an adjuvant and/or a pharmaceutically acceptable carrier. Specific embodiments of the method of the invention relate to antigen preparations comprising preparations of *H. felis* and/or *H. bizzozeronii* and/or *H. cynogastricus*. More specifically, the antigen preparation used comprises a lysate of one or more of these bacteria, but alternative embodiments include antigen preparations comprising live-attenuated bacteria or processed and/or artificial bacterial preparations. The methods of the invention may comprise intranasal or subcutaneous administration of the vaccine of the invention.

Yet a further aspect of the invention relates to an animal model for Candidatus *Helicobacter suis* infection, more particularly a mouse model. This model allows the in vivo propagation of Candidatus *Helicobacter suis* in an animal other than its natural host. This model is obtained according to the invention by infecting a mouse with Candidatus *Helicobacter suis*-infected material. More particularly this comprises isolating cells from the stomach wall of a pig infected with Candidatus *Helicobacter suis*, optionally making a homogenate thereof, and intragastrically infecting mice with the cells or homogenate. The infection in the mice and the effect of vaccination can be followed up by faecal PCR.

A further aspect of the invention relates to an isolated bacterium of the species *Helicobacter cynogastricus* deposited under Accession Number LMG P-23100. The invention further relates to the use of *Helicobacter cynogastricus* in the production of a vaccine.

DETAILED DESCRIPTION OF THE INVENTION

The present invention will be described with reference to certain embodiments and to certain Figures but the present invention is not limited thereto but only by the claims.

The present invention relates to the vaccines and vaccination methods against *Helicobacter* spp., more particularly against Candidatus *Helicobacter suis*. The present invention relates to the use of antigens and antigen preparations of certain *Helicobacter* species for vaccinating animals, especially livestock (cows, sheep, horses, . . . ), more particularly swine, most particularly cultivated pigs, which are infected with or susceptible to infection with *Helicobacter* spp., more particularly with Candidatus *Helicobacter suis*. Also other animals, such as, but not limited to humans, monkeys, rabbits, rodents, cats and dogs which are suspected to be infected with *Helicobacter* spp., more particularly with Candidatus *Helicobacter suis* can be vaccinated with the antigen preparation of the present invention.

"Candidatus *Helicobacter suis*" as referred to herein is a bacterium which was previously known as "*H. heilmannii*" type I (Trebesius et al. (2001) *J Clin Microbiol.* 39, 1510-1516. It is now accepted that "*H. heilmannii*" type 1 is identical to "Candidatus *H. suis*" (O'Rourke et al. (2004) *Int J Syst Evol Microbiol.* 54, 2203-2211; De Groote et al. (1999) *Int. J. Syst. Bacteriol.* 49, 1769-1777), a spirally shaped bacterium that colonizes the stomach of more than 60% of slaughter-pigs. Candidatus *Helicobacter suis* is also defined at the molecular level as the *Helicobacter* species having a 16S rRNA sequence Genbank Accession AF 127028 (D. De Groote et al. (1999) cited above) and AF506788-92 (O'Rourke et al. (2004) cited above) and a urease gene sequence as depicted in Genbank Accession AF508013-AF508014 (O'Rourke et al. (2004) *Int J Syst Evol Microbiol.* 54, 2203-2211).

The bacterial species suitable for the purpose of the invention are bacteria other than Candidatus *Helicobacter suis* of the *Helicobacter* genus, most particularly species that are related to but not identical to Candidatus *Helicobacter suis*. The phrase "related to" in the context of bacterial species is used herein to indicate a phylogenetic relation, preferably expressed by molecular biology parameters. More generally the bacteria related to Candidatus *Helicobacter suis* have a 16S rRNA sequence which is at least 75%, 80%, 85%, 90%, 93%, 95%, 98% 99% identical with the 16S rRNA sequence of Candidatus *Helicobacter suis*. Or expressed in an alternative way, the bacteria related to Candidatus *Helicobacter suis* comprise an urease coding sequence having a sequence which is at least 75%, 80%, 85%, 90%, 95%, 98% 99% identical at the DNA level with the urease sequence of Candidatus *Helicobacter suis*. Species that are identified as 'closely related to Candidatus *Helicobacter suis*', based on the above criteria (with a 16S rRNA sequence having at least about 93% to 99%, sequence identity with Candidatus *Helicobacter suis*), can nevertheless be identified as a different species based on other criteria such as, but not limited to, whole-cell protein profiles, as described herein. The reference sequence of 16S rRNA of Candidatus *Helicobacter suis* corresponds to that of Genbank Accession AF 127028.

"Antigen preparation" as used in the context of the present invention relates to a composition comprising at least one protein or fragment thereof which provokes an immune response (hereafter referred to as 'antigen') when administered to an animal. For use as a vaccine in the context of the present invention the antigen preparation may comprise whole-killed (inactive) bacteria, live-attenuated (weakened) bacteria or processed and/or artificial bacterial preparations or combinations thereof. Processed bacterial preparations included preparations of bacterial proteins which are partially or completely purified and/or pretreated. Examples of artificial bacterial preparations include protein preparations either in part or entirely obtained by synthetic or recombinant methods.

According to certain embodiments the antigen preparations used for vaccination according to the present invention comprise one or more antigens obtained from different *Helicobacter* species which are related to Candidatus *Helicobacter suis*. Examples of suitable antigens include but are not limited to the urease enzyme, heat shock proteins, cagA and vacA.

A "vaccine" as used herein refers to a composition such as the antigen preparation described herein which is administered to stimulate an immune response that will protect a person from illness due to that agent. The vaccine of the present invention is intended for use both as a therapeutic (treatment) vaccine, i.e. for administration to the animal after infection with the intention to reduce or arrest disease progression and as a preventive (prophylactic) vaccine, for administration to the animal prior to infection, with the intent to prevent initial (and/or recurrent) infection.

The vaccination protecting against one species using antigens from another species is referred to as "cross-vaccination" or "heterologous vaccination".

The present invention is based on the observation that mucosal and parenteral vaccination with heterologous antigens from *H. pylori* SS1 or *H. felis* CS1 elicited a significant reduction in bacterial burden but not sterilizing immunity upon "Candidatus *H. suis*" challenge. Phylogenetically, *H. felis* is more closely related to "Candidatus *H. suis*" than *H. pylori* (De Groote et al. (1999) cited above), therefore one could expect to obtain better results with heterologous *H. felis* immunization. The present invention demonstrates that only minor non-significant differences in the level of protection between these two groups are found.

The invention thus relates to heterologous vaccination, i.e. the use of an antigen preparation of a species related to Candidatus *H. suis*, to obtain protection against infection by *Helicobacter* spp., more particularly by Candidatus *H. suis*.

The object of the vaccine and vaccination therewith according to the present invention includes obtaining complete protection (sterilizing immunity) against *Helicobacter* spp., more particularly against Candidatus *Helicobacter suis* in an animal but also reducing the bacterial burden of *Helicobacter* spp., more particularly of Candidatus *Helicobacter suis* by at least 25, 40, 60, 80% compared to prior to vaccination and/or compared to animals which have not received the vaccine of the present invention and are/have been subjected to the same infectious agent. Most particularly, the present invention relates to vaccines and vaccination strategies which ensure a protective effect or reduced bacterial burden for a prolonged period of time, such as during at least 4, 6, 10, 12 or more than 12 weeks.

Identification and quantification of such infection and/or bacterial burden in an animal can be done in a number of ways. Classically, this is done by determining the presence of the infectious agent, or a protein or DNA sequence thereof in a sample of body fluid or in urine or faeces. Alternatively, the reaction of the immune system, e.g. the presence of antibodies to the infectious agent, can be measured. According to a particular embodiment of the invention accurate diagnosis and quantification of *Helicobacter* infection is obtained by identification of Candidatus *H. suis* DNA, e.g. by PCR as described in the art (Fox and Lee (1997) *Lab. Anim. Sci.* 47, 222-255). Since "Candidatus *H. suis*" is hitherto uncultivable, a quantitative urease test is use to quantify this species. This assay has been used in the prior art to quantify *H. heilmannii*, *H. felis* and *H. pylori* infection in mouse immunisation studies (Michetti et al. (1994) *Gastroenterology* 107: 1002-1011; Kleanthous (2001) *Vaccine* 19, 4883-4895; Saldinger et al. (1998) *Gastroenterology* 115, 891-897). This urease test was found to be less sensitive than determining the number of bacteria after cultivation.

According to a first aspect, an antigen preparation of one or more species related to Candidatus *H. suis* is used to obtain prophylactic or therapeutic immunity to Candidatus *H. suis*. More particularly, the invention relates to antigen preparations of one or more species having at least 93% sequence identity in the 16S rRNA or urease protein sequence to Candidatus *H. suis*. According to particular embodiments of the present invention the species related to Candidatus *Helicobacter suis* is/are species selected from the group of *H. pyloris, H. bizzozeronii, H. felis* and *H. salomonii*. Other suitable *Helicobacter* species are *H. bilis, H. fenelliae, H. pametensis, H. nemestrinae, H. acinonychis, H. pullorum, H. mustelae, H. hepaticus, H. cinaedi* and *H. canis*.

The present invention further provides a particular embodiment of a strain useful for the vaccination against Candidatus *H. suis*, i.e. *H. cynogastricus*, as described in the Examples herein.

According to a particular embodiment, the antigen preparation is a cell lysate, i.e. a mixture obtained upon lysis of bacterial cells. A particular example of a bacterial cell lysate is the soluble fraction of a sonicated bacterial culture, e.g. obtained after filtration. Alternatively or in addition, bacteria can be fragmented using a high-pressure homogenizer (e.g. Avestin model EmulsiFlexC5) Optionally, the cell lysate is further inactivated by treatment with formalin, or a comparable agent. Generally not all proteins in a lysate will provoke an immune response. Alternatively, the antigen preparation according to the present invention is obtained by fractionation and/or purification of one or more proteins from a lysate or bacterial culture medium to obtain a composition of enriched or purified antigens. Also falling within the concept of the present invention are recombinant proteins or fragments thereof used as antigen preparation. Most particular examples of isolated, purified and/or recombinant bacterial proteins suitable in the context of the present invention are heat shock proteins and/or urease proteins.

The vaccine of the present invention optionally contains only the antigen preparation of the invention. Alternatively, the vaccine can comprise, in addition to the antigen preparation of the present invention, a suitable adjuvant. The type of adjuvant will vary, depending on the type of antigen preparation and route of administration used. According to a particular embodiment of the present invention the antigen preparation which is a sonicated antigen solution is administered intranasally with Cholera toxin (CT) or subcutaneously with saponine as adjuvant. Any adjuvant known in the art may be used in the vaccine composition, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01K2), the "Iscoms" of EP 109 942, EP 180 564 and EP 231 039, aluminum hydroxide, saponin, DEAE-dextran, neutral oils (such as miglyol), vegetable oils (such as arachis oil), liposomes, Pluronic® polyols. Adjuvants include, but are not limited to, the RIBI adjuvant system (Ribi Inc.), alum, aluminum hydroxide gel, cholesterol, oil-in water emulsions, water-in-oil emulsions such as, e.g., Freund's Complete and Incomplete Adjuvants, Block co-polymer (CytRx, Atlanta Ga.), SAF-M (Chiron, Emeryville Calif.), AMPHIGEN® adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *E. coli* (recombinant or otherwise), cholera toxin, or muramyl dipeptide, among many others. According to a particular embodiment recombinant mutant of *Escherichia coli* heat-labile toxin is added to the antigen preparation prior to injection into the animal.

According to another aspect, the present invention relates to the use of the vaccines of the present invention to obtain prophylactic or therapeutic immunity to *Helicobacter* spp. such as those referred to herein, more particularly to Candidatus *H. suis*.

According to a first embodiment the invention provides antigen preparations for use in prophylactic vaccination which ensure protection against *Helicobacter* spp., more particularly against Candidatus *H. suis* which is more than transient. Transient infection of prophylactically immunized mice has only been reported once in the *H. pylori* model (Garhart et al. 2002, Infect. Immun. 70:3529-3538). The present invention shows the evolution of protection over time. This is performed by a method for detection of infection in faecal samples, particularly developed for this purpose. A PCR is carried out on faecal samples collected at subsequent time points, which gives an impression of the colonization in the stomach with "Candidatus *H. suis*". The PCR reaction is performed on a small fragment of the 16S rRNA gene. Typically, this fragment has a length of less than 400 by (e.g. a fragment between 200 and 400 bp, a fragment between 200 and 100 by or a fragment between 100 and 50 bp), more particularly a fragment which comprises sequences for PCR amplification that are species-specific. This allows the detection of degraded 16S rRNA of a specific *Helicobacter* species in faecal samples. Larger fragments or full length 16S rRNA, such as detected in gastric samples (De Grootte et al (2000) cited above), could not be detected in faecal samples of pigs. It is demonstrated herein that there is a decrease in excretion of *Helicobacter* DNA from one week after infection in the immunized mice compared to the non-immunized mice, and that colonization in immunized mice never reaches the same level as in non-immunized mice.

In another aspect the present invention relates to methods for therapeutic immunization, when the organisms have already orientated the host immune response to their benefit.

The antigen preparations or vaccines of the present invention can be administered via any suitable route, such as by mucosal (intranasal), perenteral, or intramuscular administration, oral, intradermal, intraperitoneal, intravenous, or subcutaneous administration. Suitable vaccination routes also comprise combination administrations (e.g. oral/intramuscular administration). According to a specific embodiment of the invention therapeutic immunization is performed by parenteral administration of the antigen preparation of the invention. Parenteral immunization can mobilize cells from systemic origin that have not been already primed in one given direction by a *Helicobacter* infection (Guy et al. (1999) *Vaccine* 17, 1130-1135). According to another specific embodiment of the invention, intramuscular administration is used for efficient vaccination.

The antigens the present invention can be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the proteins or peptides of the present invention or the antibodies or binding portions thereof of the present invention and a carrier, for example, lubricants and inert fillers such as, lactose, sucrose, or cornstarch. In another embodiment, these compounds are tableted with conventional tablet bases such as lactose, sucrose, or corn starch in combination with binders like acacia, corn starch, or gelatin, disintegrating agents such as, corn starch, potato starch, or alginic acid, and a lubricant like stearic acid or magnesium stearate.

The antigens of the present invention may also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the antigens of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

According to yet another aspect of the invention, an in vivo animal model is provided for infection with Candidatus *H. suis*. The invention provides a method of obtaining Candidatus *H. suis* infection in a laboratory or model animal, such as mice, which method comprises intragastrically inoculating the laboratory or model animal with homogenates of cells obtained from the stomach wall of infected animals, more particularly infected pigs. According to a specific embodiment the upper cell layers and mucus are scraped from the antrum and homogenized. According to yet a further particular embodiment the material from the stomach wall of infected animals is homogenized in lyophilization medium (2 volumes of horse serum, 1 volume of BHI broth and 10% glucose) (LYM). Optionally, larger particles are removed by centrifugation. According to a particular embodiment the stomach from infected laboratory animal or model animal so obtained is again dissected and homogenized for at least two additional passages in the same animal. The infection is optionally followed up by faecal PCR as described herein.

FIGURE LEGENDS

The following Figures represent illustrative embodiments of the invention.

FIG. 1: Quantitative urease assay on gastric stomach tissue of different sites (cardia, fundus, antrum) from pigs infected with Candidatus *Helicobacter suis* from mice (n=5) and controls (n=5) according to one embodiment of the invention.

Figure 2:
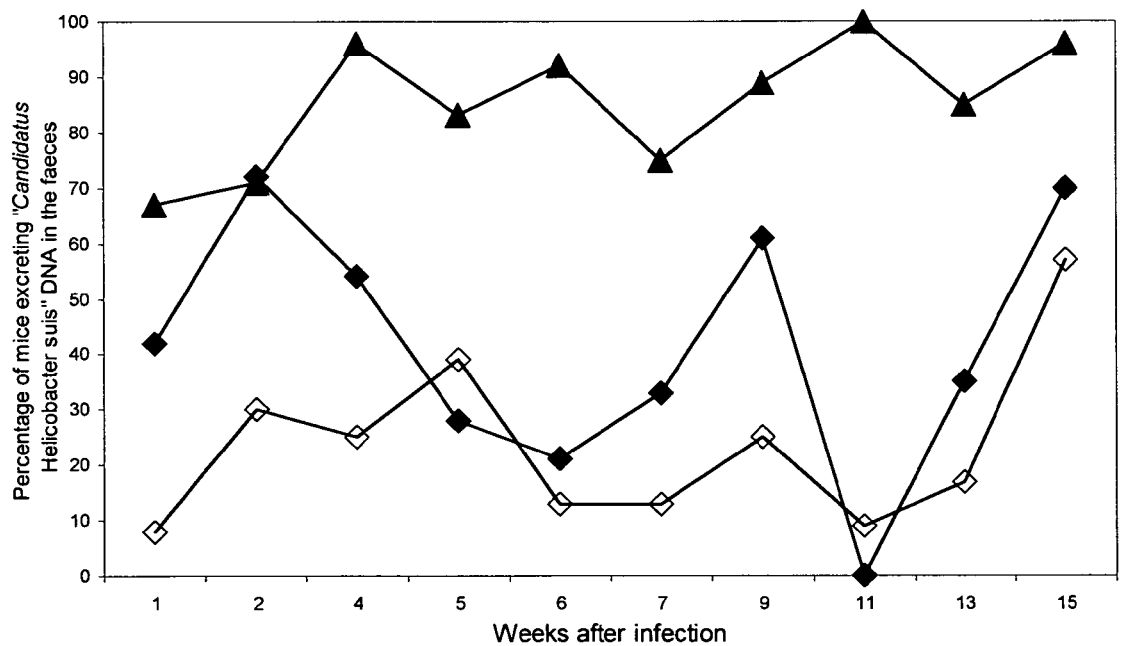

FIG. 2: Excretion of "Candidatus *Helicobacter suis*" DNA in faeces of BALB/c mice immunized intranasally with *H. pylori* antigens (♦) or *H. felis* antigens (◇) compared to unimmunized mice (▲), 1 to 16 weeks after infection with "Candidatus *Helicobacter suis*", according to one embodiment of the invention. The excretion is expressed as percentage of mice positive in PCR per group.

Figure 3:
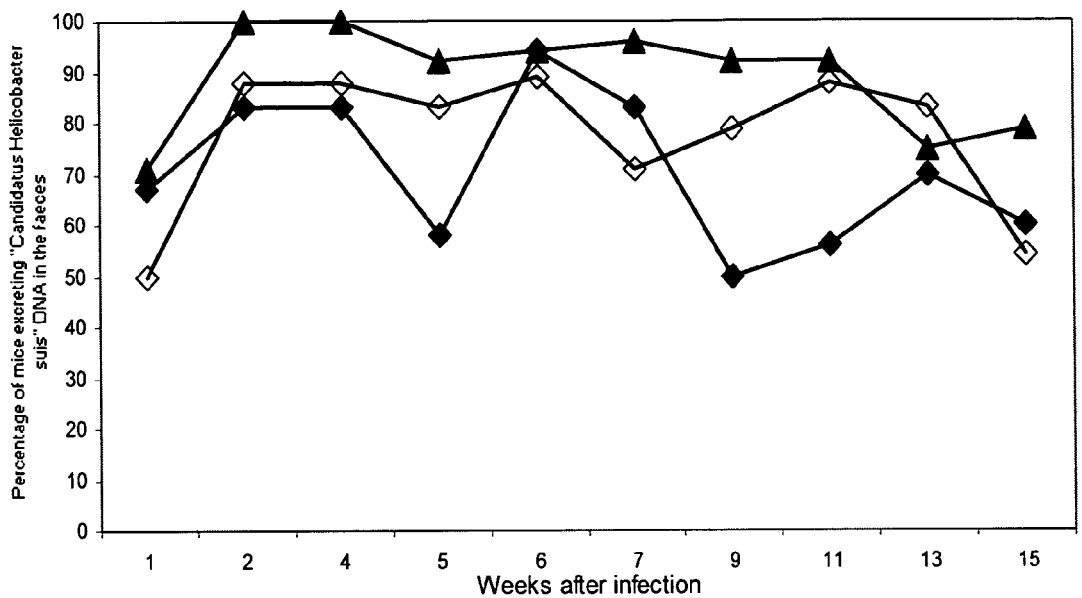

FIG. 3: Excretion of "Candidatus *Helicobacter suis*" DNA in faeces of BALB/c mice immunized subcutaneously with *H. pylori* (♦) or *H. felis* (◇) antigens, compared to unimmunized (▲) animals, 1 to 16 weeks after infection with "Candidatus *Helicobacter suis*", according to one embodiment of the invention. The excretion is expressed as percentage of mice positive in PCR per group.

Figure 4:
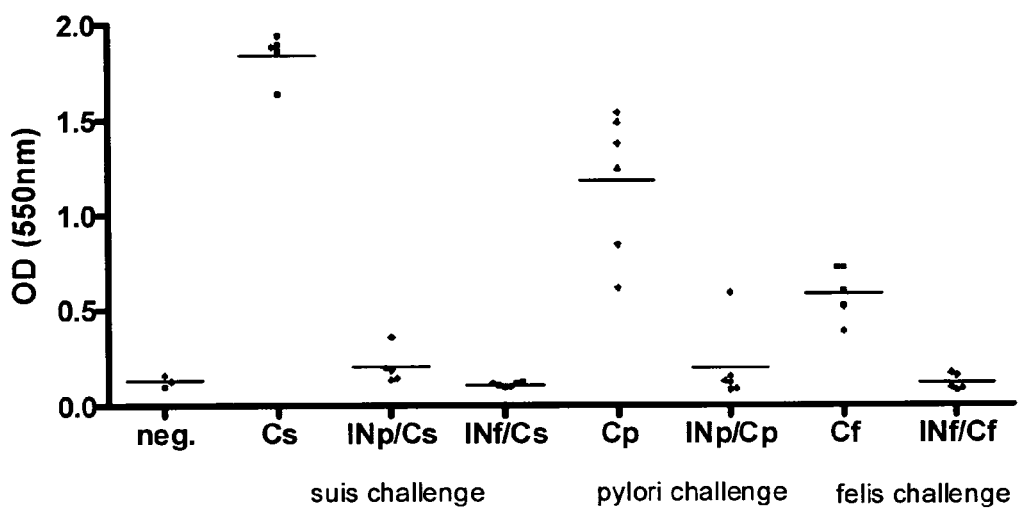

FIG. 4: Quantitative urease activity of gastric stomach tissue, represented as OD value (550 nm), from mice intranasally immunized with *H. pylori* or *H. felis* antigens according to one embodiment of the invention. Solid lines represent the geometric mean for each group studied. (Cs) animals challenge infected with "Candidatus *Helicobacter suis*"; (Cp) animals challenge infected with *H. pylori*; (Cf) animals challenge infected with *H. felis*; (IN,p) intranasal immunization with *H. pylori* antigens; (IN,f) intranasal immunization with *H. felis* antigens.

Figure 5:
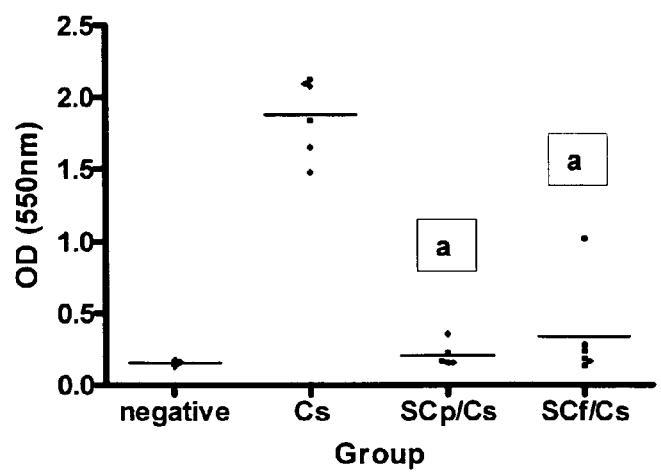

FIG. 5: Quantitative urease activity of gastric stomach tissue, represented as OD value (550 nm), from mice subcutaneously immunized with *H. pylori* (SCp) or *H. felis* (SCf) antigens according to one embodiment of the invention. Solid lines represent the geometric mean for each group studied. Significant differences ($P<0.05$) between immunized and non-immunized challenged animals, for each *Helicobacter* sp., are indicated with letter a. (Cs) animals challenge infected with "Candidatus *Helicobacter suis*".

Figure 6:
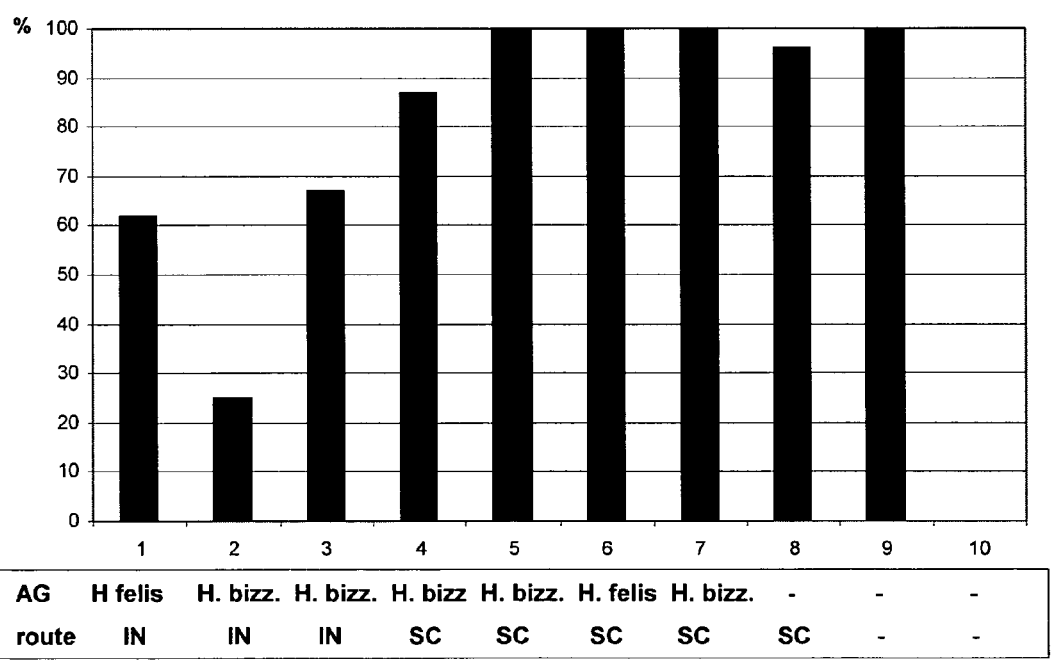

FIG. 6: Excretion of "Candidatus *Helicobacter suis*" DNA in the faeces of BALB/c mice immunized intranasally with *H. felis* CS1 or *H. bizzozeronii* antigens three weeks post "Candidatus *Helicobacter suis*" challenge according to particular embodiments of the invention. The excretion is expressed as percentage of mice positive in PCR. The differences between the experimental conditions are explained in detail in Table 1.

Figure 7:
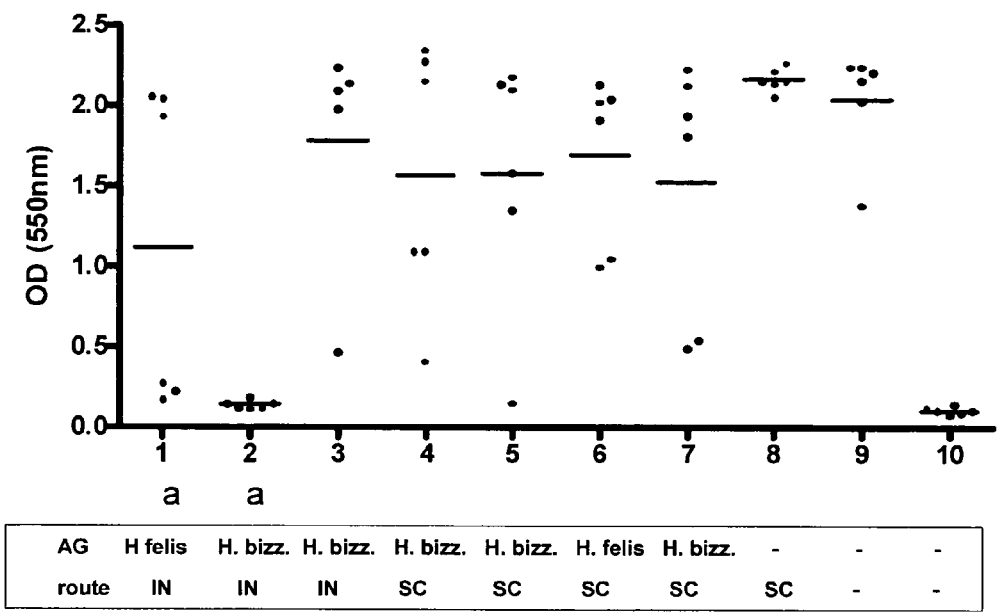

FIG. 7: Quantitative urease activity of gastric stomach tissue, represented as OD value (550 nm). Solid lines represent geometric mean for each group studied. A significant ($P<0.05$) decrease in urease activity between non-immunized, challenged (group 9) and immunized animals was found for group 1 and group 2, both representing intranasal immunization with *H. felis* CS1 sonicated antigen solution or *H. bizzozeronii* respectively (a), according to particular embodiments of the invention. The differences between the experimental conditions are explained in detail in Table 1.

Figure 8A:
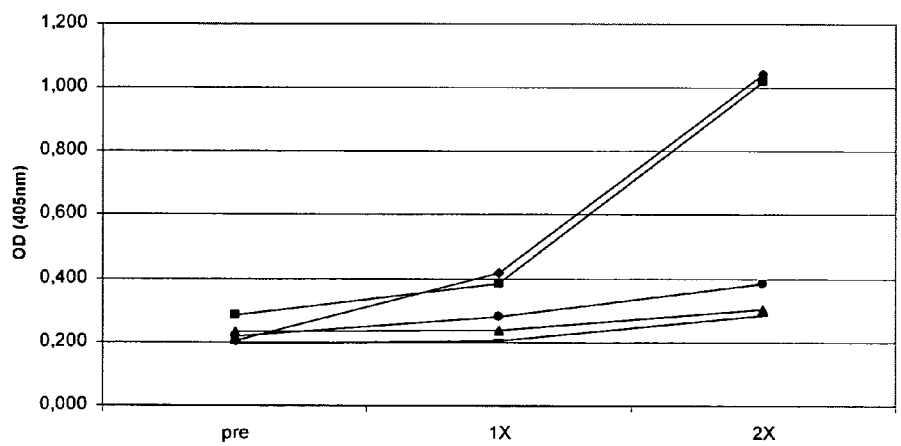

FIG. 8A: Serumconversion (s/p values) against *H. felis* antigens after vaccination with *H. felis* antigens (serology data in swine) (group 1: ■; group 2: ♦; group 3: ▲) and *H. bizzozeronii* antigens (group 4: ●) (adjuvans only: _) Pre: pre immunization; 1X: 3 weeks after the first immunization; 2X: two weeks after the second immunization.

Figure 8B:
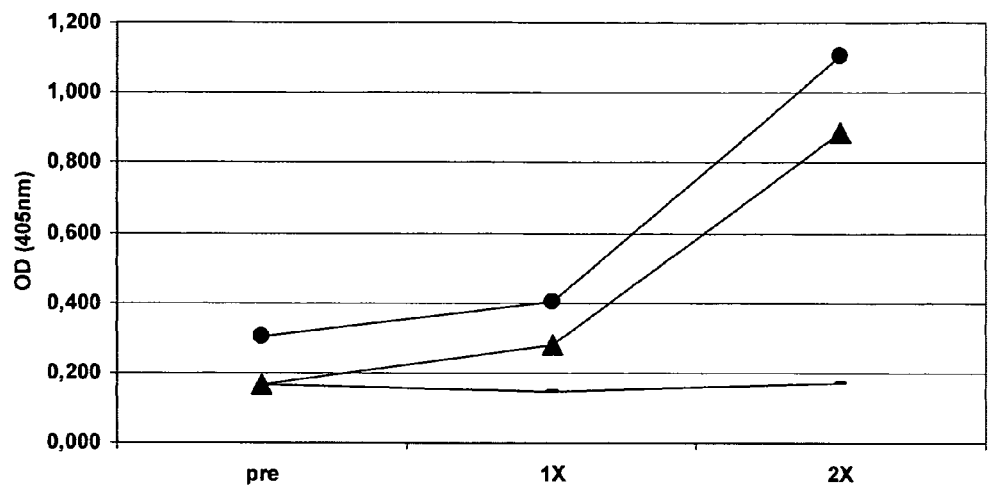

FIG. 8B: Serumconversion (s/p values) against *H. bizzozeronii* antigens after vaccination with *H. felis* antigens (group 3: ▲) and *H. bizzozeronii* antigens (group 4: ●) (adjuvans only: _) Pre: pre-immunization; 1X: 3 weeks after the first immunization; 2X: two weeks after the second immunization.

Figure 9A:
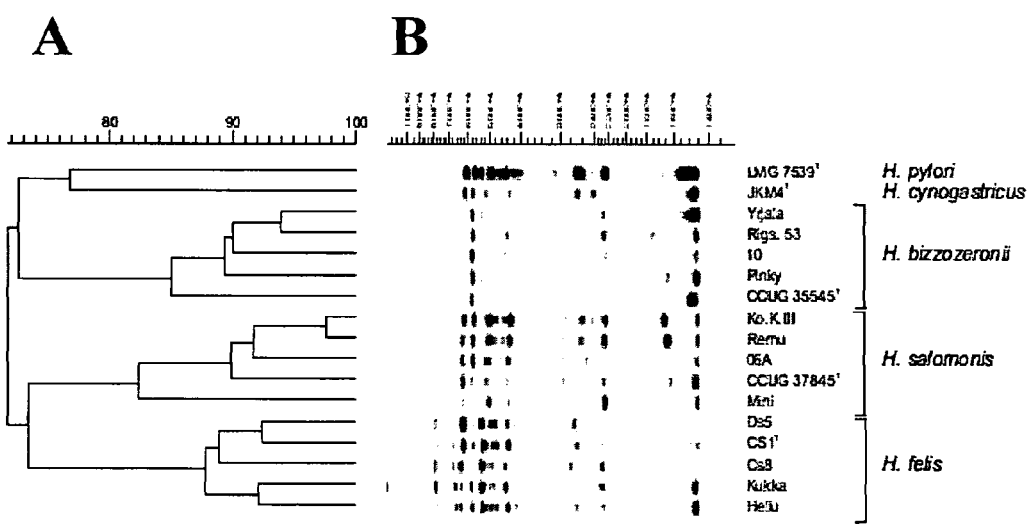

FIG. 9A: Dendrogram (A) derived from the numerical analysis of the whole-cell protein profiles (B) of *H. cynogastricus, H. pylori, H. bizzozeronii, H. salomonis* and *H. felis* reference strains.

FIG. 9B: Similarity matrix based on 16S rRNA sequence comparison.

Figure 10:
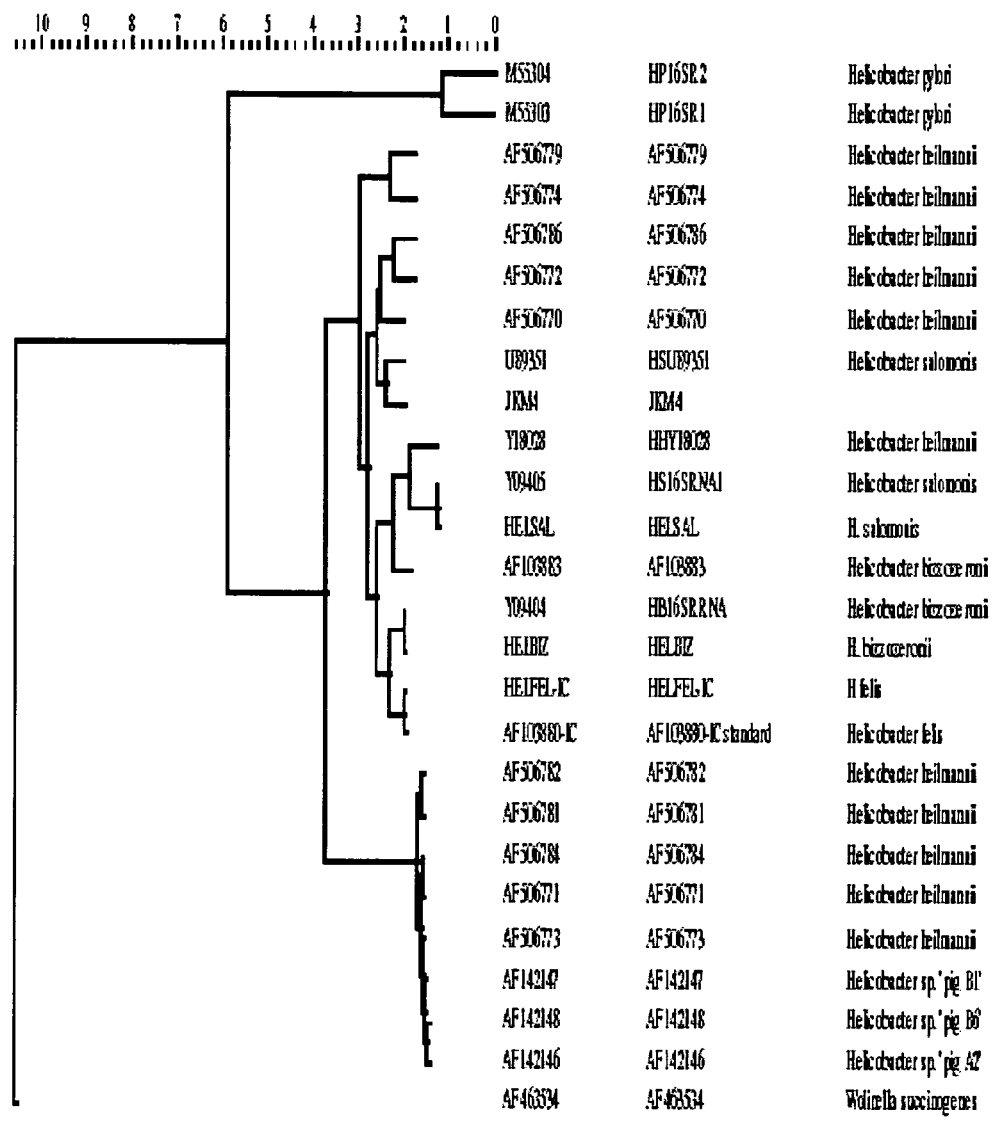

FIG. 10: Phylogenetic tree for 25 strains of *Helicobacter* species based on 16S rRNA sequence similarity. The scale bar represents a 10% difference in nucleotide sequences as determined by measuring the lengths of the horizontal lines connecting any two species.

FIG. 11: Genomic sequence of 16S rRNA gene of *Helicobacter cynogastricus*.

The invention is illustrated but not limited to the following examples.

EXAMPLES

General Methodology

Mice. All experiments involving animals were approved by the Animal Care and Ethics Committee of the Faculty of Veterinary Medicine, Ghent University. Five week-old male, SPF BALB/c mice were purchased from an authorized breeder (HARLAN, Horst, The Netherlands). The animals were housed individually in autoclaved filter top cages and provided with a commercial diet (TEKLAD, HARLAN) and water ad libitum. After an adaptation period of one week, the animals were used in the experiments.

Antigens for vaccination. *H. pylori* SS1, *H. felis* CS1 (ATCC 49179) and *H. bizzozeronii* (CCUG 35545) were grown on brain heart infusion (BHI, Oxoid, England) agar plates supplemented with 10% horse blood, 5 mg/ml amphotericin B, 10 mg/ml vancomycin, 5 mg/ml trimethoprim lactate and 2500 units/l polymyxin B (Skirrow, *Campylobacter* Selective Supplement, Oxoid) and Vitox supplement (Oxoid). Plates were incubated at 37° C. in micro aerobic conditions. The antigens used for immunization were prepared by harvesting 3-day old cultures in sterile phosphate buffered saline. The bacterial suspension was sonicated (8 times 30 seconds, 50% capacity; Misonix, Incorporated, USA). After centrifugation (5,000 g, 5 min., 4° C.) the supernatant was filtered through a 0.22-μm pore filter (Schleisser Schuell, Dassel, Germany) and stored at −70° C. Afterwards, protein concentration was determined by the Lowry assay (Lowry et al. (1951) *J. Biol. Chem.* 193, 265-275).

Formalin inactivated bacterial cultures were prepared by transferring bacterial cultures from agar plates to BHI broth supplemented with 0.2% Skirrow, 0.6% Vittox and 10% horse serum. After 24 h of incubation at 37° C. 0.5% formaldehyde was added and further incubated at 37° C. Twenty-four hours later the culture was cooled to 4° C. and checked microscopically for presence of intact bacteria. Twenty percent of sodiumbisulphite 0.166M was added to neutralize formaldehyde. Afterwards, protein concentration was determined by the Lowry assay.

Intranasal immunization. Forty-five mice were divided into seven groups of six animals (groups 1-7) and one group of three animals (group 8). All animals from groups 1 and 3 were immunized intranasally with *H. felis* CS1 and those of groups 2 and 4 with *H. pylori* SS1, twice with three weeks time interval. Intranasal immunization was done by applying about 100 μl with 100 μg of sonicated antigen solution mixed with 5 μg cholera toxin (List, Campbell, Calif., US) on the external nares of unanaesthetized mice. Mice from groups 5, 6, 7 and 8 were not immunized. Four weeks after the final immunization, all animals from groups 2 and 5 and all animals from group 1 and 6 were challenged with *H. pylori* or *H. felis* respectively, by intragastric inoculation with 0.3 ml of the bacterial suspension. This homologous vaccination experiment serves as a control. At the same time all animals from groups 3, 4 and 7 were inoculated intragastrically with "Candidatus *H. suis*". For this purpose a frozen stock from "Candidatus *H. suis*" was placed at 37° C. for 15 minutes.

During 1, 2, 4, 5, 6, 7, 9, 11, 13 and 15 weeks after challenge, faecal material was collected for three consecutive days from each individual mouse inoculated with "Candidatus *H. suis*" to screen for the presence of bacterial DNA. PCR on faecal samples was performed as described below.

Sixteen weeks after challenge, all animals were euthanized by cervical dislocation following isoflurane anaesthesia (IsoFLo, Abbot, Ill., US). From all animals, half of the stomach was used for a quantitative urease-test (Corthésy-Theulaz et al. (1995) cited above) as described below. From the other half, 2 mm² tissue samples from the fundic region were frozen (−20°) and used for PCR specific for "Candidatus *H. suis*" (samples from group 3, 4 and 7), *H. felis* (samples from groups 1 and 6) or *H. pylori* (samples from groups 2 and 5) as described below.

Subcutaneous immunization. Twenty-one mice were divided into three groups of six animals (groups 1-3) and one group of three animals (group 4). Animals from groups 1 and 2 were immunized with *H. pylori* or *H. felis* respectively, three times with three weeks time interval. For this purpose about 100 μl with 100 μg of the sonicated bacterial antigen solution was mixed in equal amounts with saponine adjuvant and injected subcutaneously at the lower back of the animals. Four weeks after the final immunization, animals from groups 1, 2 and 3 were infected with "Candidatus H. suis" as described in protocol 1. Animals from group 4 were not immunized or challenged. Sampling of faecal material, from groups 1, 2 and 3, during the experiment and sampling of stomach material from all animals, at the end of the study, was done as described in protocol 1.

Preparation of Candidatus H. suis in an in vivo system, for use in challenge experiments. Thirty pig stomachs were obtained from the slaughterhouse. The stomachs were opened and the remaining food was rinsed off with autoclaved tap water (37° C.). A small mucosal fragment from the antrum (1 cm from the torus pyloricus) was taken to screen for the presence of "Candidatus H. suis". Half of this fragment was used for rapid urease test (CUT, Temmler Pharma, Marburg, Germany, 37° C. for 1 h). The other half was frozen (−20° C.) and used for specific detection of "Candidatus H. suis" by PCR (De Groote et al. (200) J. Clin. Microbiol. 38, 1131-1135) as confirmation for the urease test. Stomachs from which the urease test give the quickest positive results were processed in the first instance. Therefore upper cell layers and mucus from the antrum were scraped. Scrapings were homogenized in lyophilization medium (2 volumes of horse serum, 1 volume of BHI broth and 10% glucose) (LYM). The homogenate was then centrifuged (5000 g, 5 min) to remove large particles. Supernatant was diluted 1/10 in LYM and intragastrically inoculated in three BALB/c mice. Two weeks later, these mice were euthanized, the stomachs were emptied and a fundus tissue sample was taken for rapid urease test. Urease positive stomachs were homogenized in LYM (5 ml LYM/stomach). After this first passage, two extra mouse passages were performed. Finally, infected mouse stomach homogenate from 15 mice was frozen at −70° C.

Preparation of H. pylori and H. felis for use in challenge experiments. H. pylori SS1 or H. felis CS1 were grown on BHI agar plates, statically at 37° C. in micro-aerobic conditions. After 3 days, bacteria were harvested, transferred to BHI broth supplemented with 0.2% Skirrow, 0.6% Vittox and 10% horse serum, and incubated statically at 37° C. in micro-aerobic conditions for 24 h. A bacterial suspension with an absorbance of 1.5 (450 nm) and an absorbance of 1.5 (660 nm) for H. pylori and H. felis respectively were consequently prepared in BHI broth, corresponding to approximately $10^7$ cfu/ml for H. pylori and $10^8$ cfu/ml for H. felis as confirmed by titration.

Statistical analysis. The presence of bacteria in faeces, as determined by PCR, was compared between the treatment groups by a generalized mixed model with PCR-positivity as binary response variable, time and treatment as categorical fixed effects and mouse as random effect. Pairwise comparisons were performed between the non-immunized group and the H. pylori and H. felis immunized groups at a global significance level of 5%, and a comparison wise significance level of 1.3% (adjusted by Bonferroni's technique with 3 comparisons).

The quantitative urease tests were compared by a fixed effects model with "OD value" as response variable and "treatment group" as fixed effect. Pairwise comparisons were performed between the treatment groups at a global significance level of 5% with again using Bonferroni's technique for multiple comparisons.

The quantitative urease tests shown in FIG. 7 were compared between the treatment groups by a Students t-test.

Example 1

Experimental Infection of Pigs with Candidatus H. suis

Five-week-old pigs (n=10) were purchased from a specific pathogen free (SPF) breeding unit negative for Candidatus H. suis and randomly divided in a control group (group A) and an infected group (group B) with 5 pigs in each group. After an adaptation period of 1 week the pigs were used in the experiment. Before inoculation with the pathogen, all pigs were treated intramuscularly with 60 mg/kg cimetidine to reduce stomach acid production and were anaesthetised. Group A was the control group and was sham inoculated (inoculum from urease negative stomachs from non-infected BALB/c mice) on day 7, day 14 and day 21. Group B was inoculated with Candidatus H. suis (a stomach homogenate of Candidatus H. suis infected mice) on day 7, day 14 and day 21. Immediately before and immediately after administration of the murine stomach homogenate, pigs were intragastrically inoculated with Brucella Broth (Becton Dickinson, Erembodegem, Belgium) supplemented with 10% fetal bovine serum and 0.75% agar, to delay the passage of the bacterial suspension through the duodenum. Prolonged exposure of the gastric mucosa to the bacteria is assumed to make the stomach more susceptible to colonization with Helicobacter bacteria.

All animals were euthanized 5 weeks after the third inoculation, and necropsied immediately. At necropsy, the stomachs were excised. The mucosal surface from the pars oesophagea was macroscopically examined and lesions were scored on a scale of 0-5 using the method of Hessing et al. (1992). (score 0=intact mucosa, score 1=mild hyperkeratosis (<50% surface area), score 2=severe hyperkeratosis (50% or more of surface area), score 3=hyperkeratosis and a few small erosions (less than 5 and shorter than 2.5 cm), score 4=hyperkeratosis and extensive erosions (more than 5 erosions and/or longer than 2.5 cm), score 5=hyperkeratosis and very large erosions (more than 10 erosions or longer than 5 cm) and/or ulcers.

In group B, inoculated with "Candidatus H. suis", three animals had a lesion score of 3, one animal a score of 4 and one animal a score of 5. In the control group, lesion scores were 2 (one animal), 3 (two animals) and 4 (two animals). The difference in lesion scores between "Candidatus H. suis" infected animals and control animals was not significant (P=0.36).

After scoring, three sites from the glandular mucosa (0.5 cm$^2$) from each stomach were sampled for PCR, quantitative urease test and histology. These three sites corresponded to the cardia (immediately adjacent to the margo plicatus), the fundus, and the antrum pyloricum (1 cm away from the torus pyloricus).

PCR for specific detection of "Candidatus H. suis" infection in gastric tissue. DNA was extracted with DNeasy Tissue Kit (Qiagen, Hilden, Germany). PCR for specific detection of "Candidatus H. suis" was performed as described by De Groote et al. (2000) cited above. The samples of all control animals were negative. All fundus and antrum samples and 3/5 cardia samples of group B were positive in PCR.

The Urease assay was performed as described by Corthésy-Theulaz et al. (1995) cited above. Mean OD-values for each sampling site are shown in FIG. 1. Significant differences (P<0.05) between control animals and animals infected with "Candidatus H. suis" were found for all tissue samples originating from the fundus and the antrum (cardia, P=0.0676; fundus, P=0.0038; antrum pyloricum P=0.0011).

There was no significant difference in mean OD value for the different sampling sites in infected animals (cardia vs. fundus P=0.2280; cardia vs. antrum pyloricum P=0.1733 and fundus vs. antrum pyloricum P=0.7824).

Histological examination was performed using a polyclonal goat anti-*H. pylori* antibody as described by De Groote et al. (2000). Animals positive for "Candidatus *H. suis*" had lesions predominantly in the antral mucosa. In this stomach region, focal lymphoplasmacytic cellular infiltrates in the mucosa were present in all 5 animals. In 3/5 infected animals antral lymphoid follicles with germinal centers were present. Due to the size of the follicles, they were associated with displacement and loss of gastric glands. In 2/5 infected animals no follicles could be detected in the antral mucosa, but these animals did show aggregates of lymphocytes and plasmacells in the lamina propria. In the fundus of "Candidatus *H. suis*" infected animals, only mild scattered infiltration of lymphocytes was present. In the antrum, colonization was present in the mucus overlying the surface epithelium and in the surface foveola, but did not extend deep into the gastric pits. Colonization of the fundic mucosa with "Candidatus *Helicobacter suis*" was detected in the glandular foveola and extended down halfway the gastric pits. Bacteria were found in close contact with gastric epithelial cells i.e. mucus producing cells and parietal cells. No bacteria were demonstrated in the stomach of the control animals. Control animals are negative for "Candidatus *H. suis*" (Group A).

Example 2

Experimental Set-Up of Comparative Immunization with Species Related to Candidatus *H. suis*

In a parallel experiment, the effect of immunization with *H. felis* or *H. bizzozeronii* sonicate, *H. bizzozeronii* or *H. felis* formaline inactivated and control adjuvants was tested using intra-nasal or subcutaneous immunization routes. Sixty mice were divided into ten groups of six animals as shown below (Table 1).

TABLE 1

Experimental design

| Group[a] | Antigen preparation[b] | Adjuvant[c] | Route[d] | Challenge |
|---|---|---|---|---|
| 1 | *H. felis* sonicate | CT | IN | "Candidatus *H. suis*" |
| 2 | *H. bizzozeronii* sonicate | CT | IN | "Candidatus *H. suis* |
| 3 | *H. bizzozeronii* formaline inactivated | CT | IN | "Candidatus *H. suis*" |
| 4 | *H. felis* sonicate | saponine | SC | "Candidatus *H. suis*" |
| 5 | *H. felis* sonicate | saponine + LT | SC | "Candidatus *H. suis*" |
| 6 | *H. felis* formaline inactivated | saponine + LT | SC | "Candidatus *H. suis*" |
| 7 | *H. bizzozeroni* sonicate | saponine + LT | SC | "Candidatus *H. suis*" |
| 8 | / | saponine + LT | SC | "Candidatus *H. suis*" |
| 9 | / | / | / | "Candidatus *H. suis*" |
| 10 | / | / | / | / |

[a]Mice were divided into 10 experimental groups (1-10).
[b]One hundred micrograms of sonicated antigen solution or formol inactivated antigens were used for each immunization.
[c]Five μg of cholera toxin was used for the intranasal immunization. For the subcutaneous immunization, antigens in solution was mixed with equal amount of saponine adjuvant and 1 μg of LT.
[d]IN, intranasally; SC, subcutaneously.

Groups 1, 2 and 3 were immunized intranasally twice with three weeks interval. Therefore 100 μg of *H. felis* or *H. bizzozeronii* sonicated proteins, mixed with 5 μg of cholera toxin (List, Campbell, Calif., US), was applied on the external nares of unanaesthetized mice.

Groups 4-7 were immunized subcutaneously three times with three weeks time interval. For this purpose 100 μg of the sonicated antigen solution was mixed in equal amounts with saponine adjuvant. Immediately prior to injection 1 μg of recombinant mutant of *Escherichia coli* heat-labile toxin (LTR192G, donated by J. Clements) was added and then the antigen preparation was injected subcutaneously at the lower back of the animals.

Animals from group 8 were immunized subcutaneously with saponine adjuvant plus LTR192G only. Mice from groups 9 and 10 were not immunized.

Four weeks after the final immunization, a frozen stock from "Candidatus *H. suis*", was placed at 37° C. for 15 minutes. All animals from groups 1-9 were challenged by intragastric inoculation with 0.3 ml of the "Candidatus *H. suis*" stock.

During the third week after challenge, faecal material was collected for four consecutive days from each individual mouse to screen for the presence of "Candidatus *H. suis*" DNA. PCR on faecal samples was performed as described below.

Six weeks after challenge, all animals were euthanized by cervical dislocation following isoflurane anaesthesia (IsoFLo, Abbot, Ill., US). From all animals, half of the stomach was used for a quantitative urease-test (Corthésy-Theulaz et al. 1995, above) as described below. From the other half, 2 mm$^2$ tissue samples from the fundic region were frozen (−20°) and used for PCR specific for Candidatus *H. suis* as described below.

Example 3

Faecal Excretion of "Candidatus *H. suis*" DNA in Faeces of Non-Immunized and Immunized Mice Detection of 'Candidatus *H. suis*' DNA in faecal samples. PCR on faecal samples was performed to evaluate the excretion of "Candidatus *Helicobacter suis*" DNA. DNA was extracted using QIAamp® DNA Stool Mini Kit (Qiagen, Hilden, Germany). Primers HS 586 gggaggacaagtcaggtgtgaa [SEQ ID:1] and HS641 tctcccacactccagaaggatag [SEQ ID:2], complementary to the 16S rRNA genes from "Candidatus *Helicobacter suis*" were used to amplify a 79-bp fragment. The specificity of the primerset was tested on DNA extracts from 17 other *Helicobacter* species and from *Campylobacter jejuni* (table 2). The sensitivity was assayed by adding cloned 16S rRNA to a fecal control sample. After DNA isolation and PCR, a fragment was obtained when about 100,000 copies were added to a control sample.

TABLE 2

| [b]Strain | Species |
|---|---|
| CCUG 38995 | *H. bilis* |
| CCUG 29260 | *H. pametensis* |
| CCUG 32350 | *H. nemestrinae* |
| NCTC 11961 | *H. pylori* |
| LMG 6444 | *C. jejuni* |
| LMG 16318 | *H. pullorum* |
| LMG 18044 | *H. mustelae* |
| LMG 16316 | *H. hepaticus* |
| LMG 18086 | *H. canis* |

TABLE 2-continued

| [b]Strain | Species |
|---|---|
| LMG 11759 | H. fenelliae |
| LMG 14378 | H. nemestrinae |
| LMG 12678 | H. pametensis |
| LMG 12684 | H. acinonychis |
| R 10t51 | H. bizzozeronii |
| R 1053 | H. salomonis |
| R 3647 | H. felis |
| LMG 7543 | H. cinaedi |

[b]Bacterial strains used for the evaluation of the Candidatus "Helicobacter suis" specific PCR on faecal samples.

PCR reaction mixtures (25 µl) contained 50 pmole of each primer (Invitrogen Life Technologies, Merelbeke, Belgium), 200 µM of each deoxynucleoside triphosphate (Amersham Pharmacia Biotech, Puurs, Belgium), 0.03 U/µl Taq platinum, 1.5 mM $MgCl_2$ and 1×PCR buffer (Invitrogen Life Technologies). PCR products were run on 1.5% agarose gels containing 50 ng/ml ethidium bromide. After 1 hour at 160V the products were visualized with an UV transilluminator. The Candidatus *Helicobacter suis* amplified fragment has a length of 80 bp. No PCR fragments are obtained using any of the other species presented in table 2.

Statistical Analysis

The presence of bacteria in faeces, as determined by PCR, was compared between the treatment groups by a generalized mixed model with PCR-positivity as binary response variable, time and treatment as categorical fixed effects and mouse as random effect. Pairwise comparisons were performed between the non-immunized group and the *H. pylori* and *H. felis* immunized groups at a global significance level of 5%, and a comparison wise significance level of 1.3% (adjusted by Bonferroni's technique with 3 comparisons).

The presence of DNA in faecal samples as determined by PCR assay, per group, and calculated for each week of sampling is depicted in FIG. 2 and FIG. 3 for experiment 1 and experiment 2 respectively. There was an overall significant difference in faecal excretion between non-immunized and intranasally immunized animals both for *H. pylori* and for *H. felis* sonicated antigen solution (P<0.0001) in that the intranasally immunized mice excreted less "Candidatus *Helicobacter suis*" DNA in the faeces in comparison to the non-immunized "Candidatus *H. suis*" challenged animals. The difference in excretion between the two intranasally immunized groups was not significant (P=0.0241).

A significant difference was found between non-immunized mice and mice immunized subcutaneously with *H. pylori* sonicated antigen solution (P=0.0001). The difference between non-immunized mice and mice immunized subcutaneously with *H. felis* sonicated antigen solution was significant at P=0.0175. There was no significant difference between the two subcutaneously immunized groups (P=0.2445).

The results of the experiment, described in Table 1, on the number of mice excreting "Candidatus *Helicobacter suis*" DNA in the faeces three weeks post challenge are shown in FIG. 6. Intranasal immunization caused a lower excretion compared to the non-immunized excreting "Candidatus *Helicobacter suis*" challenged animals. For the subcutaneously immunized groups an effect of immunization was only detectable in group 4, representing animals immunized with *H. felis* CS1 sonicated antigen solution.

Example 4

Quantitative Urease in Gastric Tissue

Quantitative Urease Test of Gastric Tissue.

The stomach sample was immersed in 500 µl of CUTest and incubated at 37° C. for 3 hours. After centrifugation (5 min, 100 g) the supernatant was used for spectrophotometric quantification at an OD of 550 nm. The assay was performed as described in Corthésy-Theulaz et al. (1995) *Gastroenterol.* 109, 115-121).

For the homologous intranasal immunization (FIG. 4) there was a significant difference (P<0.05) in urease activity between non-immunized and immunized animals both for *H. pylori* SS1 and *H. felis* CS1. Immunization of animals with *H. pylori* SS1 or *H. felis* CS1 sonicates antigen solution before "Candidatus *H. suis*" challenge resulted in a significant decrease (P<0.0001) in urease activity compared to the non-immunized challenged group. Subcutaneous immunization (FIG. 5) with *H. pylori* or *H. felis* antigens, resulted in a significant (P<0.0001) decrease in urease activity compared to the non-immunized challenged group.

In the experiment described in Table 1, the mean OD value from non-immunized non-challenged mice was 0.103. The mean OD value from non-immunized mice, challenged with "Candidatus *Helicobacter suis*" was 2.038. A significant (P<0.05) difference in urease activity between non-immunized, challenged (group 9) and immunized animals was found for group 1 and group 2, representing intranasal immunization with *H. felis* CS1 or *H. bizzozeronii* sonicated antigen solution respectively. None of the subcutaneously immunized groups showed a significant decrease in urease activity compared with group 9. In the statistical analysis, group 7, representing animals immunized subcutaneously with *H. bizzozeronii* sonicated antigen solution, showed the lowest P value (P=0.085).

Example 5

PCR Analysis of Gastric Tissue

PCR Analysis of Gastric Tissue.

DNA of the stomach sample was extracted with DNeasy Tissue Kit (Qiagen). PCR for detection of "Candidatus *H. suis*", *H. felis* or *H. pylori* were performed as described previously (De Groote et al. (2000) cited above and De Groote (2001) *J. Clin. Microbiol.* 39, 1197-1199).

None of the animals immunized intranasally with *H. felis* CS1 sonicated antigen solution, followed by *H. felis* CS1 challenge contained Candidatus *Helicobacter suis* DNA. In contrast, immunization with *H. pylori* SS1 and homologous challenge all showed the presence of Candidatus *Helicobacter suis* DNA in stomach samples. After heterologous intranasal and subcutaneous immunization of mice with *H. pylori* or *H. felis* antigens, and challenged with "Candidatus *H. suis*", all stomach samples contained Candidatus *Helicobacter suis* DNA.

In the experiment described in Table 1, all animals from group 10 were negative in the PCR test specific for "Candidatus *Helicobacter suis*". From the challenged animals only one animal from group 7 was negative in PCR test.

Example 6

Seroconversion in Pigs Upon Immunization with *H. felis* or *H. bizzozeronii*

30 conventional pigs of 5 weeks old (Agrivet Merelbeke), were divided into groups of 6 animals. All groups were immunized twice intramuscularly, with a three week interval, using 0.5 mg of antigens (bacterial lysate) (group 1-4) or using adjuvans only (5). Preliminary experiments with 0.1, 0.5 and 1 mg of antigen preparation showed that a dosis of 0.5 mg provoked the largest immune response.

Table 3. Immunization Scheme for Serumconversion

TABLE 3

Immunisation scheme for serumconversion

| Group | Antigen preparation | Species | additives |
|---|---|---|---|
| 1 | 0.5 mg sonicated bacterial lysate | *H. felis** | |
| 2 | 0.5 mg sonicated bacterial lysate | *H. felis* | CT (Cholera Toxin) |
| 3 | 0.5 mg sonicated bacterial lysate (formol inactivated) | *H. felis* | CT |
| 4 | 0.5 mg sonicated bacterial lysate | *H. bizzozeronii* | CT |
| 5 | Adjuvans only | | CT |

**H. felis* strain ATCC 49179*

Preserum was collected from all animals. Two weeks after the first immunization, prior to the second immunization, blood was collected. Blood was further collected after one, two and three weeks after the second immunization.

ELISA plates were coated with bacterial lysate and used for incubation with serum. Bound antigens were detected with alkaline phosphatase labelled polyclonal goat anti swine antibodies. The results are depicted in FIGS. 8a and 8b wherein ELISA results are depicted for plates respectively coated with *H. felis* and *H. bizzozeronii*.

Using ELISA plates coated with *H. felis*, serumconversion could only be demonstrated in mice immunized with *H. felis* antigens. With plates coated with *H. bizzozeronii* serumconversion could be demonstrated against *H. bizzozeronii*.

Example 7

Identification of *Helicobacter cynogastricus*

A *Helicobacter* species related to Candidatus *H. suis* and suitable for the preparation a vaccine is a novel *Helicobacter* species *Helicobacter cynogastricus* (also designated in the present invention as strain JKM4$^T$), which is a Gram-negative, microaerophilic helical-shaped rod.

Isolation of JKM4T

A *Helicobacter* strain (JKM4$^T$) was isolated from the antrum and fundus region of the stomach of a euthanized dog at the Faculty of Veterinary Medicine, Ghent University, Belgium. Samples were handled as described by Gruntar et al. (2003) *Int J Med Microbiol* 293, 65. Bacteria were grown on brain heart infusion agar (BHI; Oxoid, Ltd., Basingstoke, England), containing 10% (vol/vol) horse blood, 5 mg/l amphotericin B (Fungizone; Bristol-Myers Squibb, Epernon, France), *Campylobacter* selective supplement (Skirrow, Oxoid; containing 10 mg/l vancomycin, 5 mg/l trimethoprim lactate and 2500 U/l polymyxin B), and Vitox supplement (Oxoid). Plates were incubated with lids, uppermost at 37° C., under humidified micro-aerobic conditions in a closed circuit, created by evacuating 80% of the normal atmosphere and introducing a gas mixture of 8% $CO_2$, 8% $H_2$ and 84% $N_2$.

Plates were checked every two days and BHI broth was added on the agar surface to ensure plates would not dry up. Primary growth occurred after 10 days of incubation as an oily aspect on the broth covering the agar medium. Light microscopical examination of the broth revealed the presence of spiral-shaped, motile organisms. Gram staining proved the Gram negativity and the helical shape of the isolate. Bacterial growth of subcultures occurred as a spreading layer on moist agar plates. Pinpoint colonies were observed when an abundant amount of bacteria was brought on a dry agar surface. Bacteria grown on a dry agar mostly lost their spiral morphology and transformed to coccoid forms.

Bacteria with typical spiral morphology were harvested in BHI broth and stored at −70° C. in a medium consisting of 7.5 g glucose, 25 ml BHI (Oxoid) and 75 ml sterile inactivated horse serum. The isolated strain JKM4T is a novel helicobacter species, *Helicobacter cynogastricus* (see below) and has been deposited on Jun. 6, 2005 with Accession Number LMG P23-100 at the Belgian Coordinated Collections of Micro-organisms (BCCM™/LMG) [Laboratorium voor Microbiologie, Universiteit Gent (RUG), K. L. Ledeganckstraat 35, 9000 Gent, Belgium] by Katleen van den Buick.

Phenotypic Studies

For scanning and transmission electron microscopic examination, bacterial cultures were fixed in 2.5% glutaraldehyde and 2% paraformaldehyde in cacodylate buffer (0.1 M, pH 7.3). They were postfixed in 1% (w/vol) osmium tetroxide in distilled water. Samples for scanning electron microscopy were dehydrated in alcohol and acetone for subsequent critical point drying in liquid carbon dioxide, glued with carbon cement on aluminium stubs, sputtered with a gold layer and examined with a Philips 501 SEM. Samples for transmission electron microscopy were block stained with 2% (wt/vol) uranyl acetate in distilled water and dehydrated in ethanol. They were embedded in Epon-Spurr's (1:1) medium. Ultrathin sections were cut from samples in which bacteria were demonstrated, stained with lead citrate and examined with a Philips EM 208S. Biochemical and tolerance tests were carried out as recommended by Dewhirst et al. (2000) *Int J Syst Evol Microbiol* 50, 2231-2237, for the description of new species of the genus *Helicobacter*. The isolate was tested for oxidase, catalase (with 3% hydrogen peroxide) and rapid urease activity, and for hydrolysis of indoxyl acetate. The bacteria were also subjected to API Campy test strips (Biomerieux SA, Marcy-l'Etoile, France), which include tests for urease activity, nitrate reductase activity, esterase activity, hippurate hydrolysis, gamma-glutamyl transpeptidase activity, alkaline phosphatase activity, triphenyltetrazolium chloride (TTC) reduction, and pyrrolidonyl, L-arginine, and L-aspartate arylamidase activity.

Tolerance to 1% glycine (Merck, Darmstadt, Germany) and 1.5% NaCl (Merck) was tested on tryptic blood agar base (Oxoid) supplemented with 10% horse blood, as recommended by the Cape Town protocol for Campylobacteriaceae and *Helicobacters*. Tolerance to ox bile was tested by plating the bacteria on unsalted MacConkey agar (Oxoid).

Susceptibility to metronidazole, ampicilline, clarithromycin, tetracyclin, enrofloxacin, lincomycin, tylosin, neomycin, spectinomycin and gentamicin was tested through the agar dilution method, using Mueller-Hinton agar (Oxoid) supplemented with 10% horse blood, as previously described (Van den Bulck et al. (2005b) *Antimicrob Agents Chemother* 49, 2997-3000). All antibiotics were supplied by Sigma (St.

Louis, Mo., USA) as standard powders with known potencies, except for enrofloxacin, purchased from Bayer (Brussels, Belgium). All growth and tolerance test preparations were incubated for 7 days in a micro-aerobic atmosphere at 37° C.

Growth of the organism was tested on BHI blood agar, Brucella blood agar (Oxoid) and Mueller-Hinton blood agar. Growth at 25, 30, 37, and 42° C. was determined on BHI blood agar. These media were incubated for 7 days in a micro-aerobic atmosphere at 37° C. In addition, growth on blood-supplemented BHI agar was tested in an aerobic, aerobic with 5% $CO_2$, micro-aerobic and an anaerobic environment.

For polyacrylamide gel electrophoresis (PAGE) of whole-cell proteins, strain JKM4$^T$ (*Helicobacter cynogastricus*) was grown on Mueller-Hinton agar (Oxoid) supplemented with 5% (vol/vol) horse blood and was incubated at 37° C. in a microaerobic atmosphere containing approximately 5% $O_2$, 3.5% $CO_2$, 7.5% $H_2$, and 84% $N_2$. A whole-cell protein extract was prepared and sodium dodecyl sulphate PAGE was performed as described previously (Pot, et al. (1994) *J Appl Bacteriol* 77, 362-369). Whole-cell protein profiles of *H. bizzozeronii*, *H. salomonis* and *H. felis* reference strains and of type and reference strains of other *Helicobacter* species were available from previous studies. The densitometric analysis, normalization and interpolation of the protein profiles, and numerical analysis were performed using the GelCompar software package version 4.2 (Applied Maths, Sint Martens Latem, Belgium). The similarity between all pairs of traces was expressed by the Pearson product moment correlation coefficient presented as percentages of similarity.

Genotypic Analysis

Genomic DNA was extracted using the DNeasy Tissue kit (Qiagen, Venlo, The Netherlands) according to the instructions of the manufacturer.

The 16S rRNA gene was amplified using primers complementary to the conserved edges. Consensus primers alpha-beta-NOT (5'-TCA MC TAG GAC CGA GTC) [SEQ ID NO:3] and omega-MB (5'-TAC CTT GTT ACT TCA CCC CA) [SEQ ID NO:4] were used, as previously described (Baele et al. (2001) *J Appl Microbiol* 91, 488-491). A 1500 bp amplicon [SEQ ID NO: 5] encoding a part of 16S rRNA (FIG. 11) was amplified and sequenced using primer pD (5'-GTA TTA CCG CGG CTG CTG-3') [SEQ ID NO:6], primer gamma* (5'-CTC CTA CGG GAG GCA GCA GT-3') [SEQ ID NO:7], primer 3 (5'-GTT GCG CTC GTT GCG GGA CT-3') [SEQ ID NO:8] and primer O* (5'-MC TCA MG GM TTG ACG G-3') [SEQ ID NO:9], as described elsewhere (Coenye et al. (1999) *Int J Syst Evol Microbiol* 49, 405-413). Sequence analysis was performed using the ABI Prism™ 3100 Genetic Analyzer (Applied Biosystems, Lennik, Belgium) and sequences were compared with Genbank using the BLAST algorithm. Phylogenetic analysis was performed using KODON (Applied Maths, Sint-Martens-Latem, Belgium). Pairwise alignment homologies were calculated and a dendrogram was constructed using the neighbour-joining method.

For the detection of the urease gene, a PCR with primers U430f (5'-ckgawttgatgcaagaagg-3') [SEQ ID NO:10] and U1735r (5'-cttcgtgrattttaarrccaat-3') [SEQ ID NO:11] was performed. This PCR results in an amplicon of 1224 bp in *H. felis*, *H. bizzozeronii*, *H. salomonis* and "*Candidatus H. heilmannii*" (O'Rourke et al. (2004) *Int J Syst Evol Microbiol* 54, 2203-2211). A PCR with primers Hh2f and Hh2r which specifically amplifies a part of the urease gene of "*Candidatus H. heilmannii*" was also applied (O'Rourke et al. (2004) cited above). DNA from "*Candidatus H. heilmannii*" served as positive control, while highly purified water was included as negative control. PCR products were separated through gel electrophoresis as previously described (Baele et al. (2004) *J Clin Microbiol* 42, 1115-1122). Additionally, obtained PCR products for "*Candidatus H. heilmannii*" and JKM4T (*Helicobacter cynogastricus*) were sequenced using the BigDye Terminator Cycle Sequencing Kit (Perkin Elmer, Applied Biosystems) on a ABI Prism™ 3100 Genetic Analyzer (Applied Biosystems). The electropherograms were exported and converted to Kodon (Applied Maths) and sequences were compared with Genbank using BLAST.

tRNA intergenic length polymorphism analysis (tDNA-PCR) was performed with a consensus primer T3B (5'-AGG TCG CGG GTT CGA ATC C-3') [SEQ ID:12] (labeled with the fluorescent marker TET) and primer HT135R (5'-ACC AAC TGG GCT AAG CGA CC-3') [SEQ ID NO:13], a specific primer complementary to the tRNA intergenic spacer of *Helicobacter* species, as described earlier (Baele et al., 2004 cited above). DNA extracted from pure cultures of *H. felis*, *H. salomonis* and *H. bizzozeronii* served as positive controls, while highly purified water was included as negative control. The PCR products were separated by means of capillary electrophoresis using the ABI Prism™ 3100 Genetic Analyzer (Applied Biosystems, Lennik, Belgium). Lengths were determined by interpolation with an internal size standard mixture of GeneScan 500 ROX (Applied Biosystems) and GeneScan 400-HD ROX (Applied Biosystems), using GeneMapper (Applied Biosystems).

To determine the prevalence of the new *Helicobacter* species in cats and dogs, gastric samples were collected from the corpus region of 110 dogs (65 male, 45 female, age ranging from 1 day to 18 years) and 43 cats (25 male, 18 female, aged from 7 weeks to 18 years), from various breeds, which were presented for autopsy at the Department of Pathology (Faculty of Veterinary Medicine, Ghent University) between November 2001 and September 2003 with various pathology. DNA was extracted from the feline and canine samples using the DNeasy tissue kit (Qiagen), according to the instructions of the manufacturer. These DNA samples were subjected to tRNA intergenic length polymorphism analysis.

Phenotypic studies The salient tests that distinguish the new isolate from other canine gastric helicobacters are listed in Table 4.

TABLE 4

Characteristics of JKM4 (*Helicobacter cynogastricus*) and related gastric *Helicobacters*

| Characteristic | H. cynogastricus | H. felis | H. bizzozeronii | H. salomonis | H. pylori |
|---|---|---|---|---|---|
| Cell length (μm) | 10-18 | 5-7.5 | 5-10 | 5-7 | 2.5-5 |
| Cell width (μm) | 0.8-1.0 | 0.4 | 0.3 | 0.8-0.12 | 0.5-1.0 |
| Periplasmic fibrils | + | + | − | − | − |
| Location of the flagella | bipolar | bipolar | bipolar | bipolar | polar |

TABLE 4-continued

Characteristics of JKM4 (*Helicobacter cynogastricus*) and related gastric *Helicobacters*

| Characteristic | H. cynogastricus | H. felis | H. bizzozeronii | H. salomonis | H. pylori |
|---|---|---|---|---|---|
| No. of flagella | 6-12 | 14-20 | 10-20 | 10-23 | 4-8 |
| Flagellar sheath | + | + | + | + | + |
| Catalase activity | + | + | + | + | + |
| Oxidase activity | + | + | + | + | + |
| Urease activity | + | + | + | + | + |
| Nitrate reduction | + | + | + | + | − |
| Hippurate hydrolysis | − | − | − | − | − |
| Indoxyl acetate hydrolysis | − | − | + | + | − |
| γ-Glutamyl aminopeptidase | + | + | + | + | + |
| TTC reduction | + | − | + | + | + |
| Alkaline phosphatase activity | + | + | + | + | + |
| Growth at | | | | | |
| 25° C. | − | − | − | − | − |
| 37° C. | + | + | + | + | + |
| 42° C. | − | − | + | − | − |
| Tolerance to | | | | | |
| 1% ox bile | − | − | − | − | − |
| 1.5% NaCl | − | − | − | − | − |
| 1% glycine | − | − | − | − | − |

The ultrastructural studies of strain JKM4$^T$ (*Helicobacter cynogastricus*) revealed large spiral cells which were 10 to 18 µm long and approximately 1 µm wide, with three to eight spirals per cell. One periplasmic fibril was present at every bacterial cell, running along the external side of the helix. Up to 12 sheathed flagella were detected at both ends of each cell and these flagella were slightly off-centre. The flagellae were blunt-ended and the terminal diameter was wider than the average diameter of the flagellar body. Coccoid forms were observed in older cultures. The ultrastructural characteristics of the organisms were examined several times after several subcultures and were the same in all studies.

The isolate presented oxidase, urease and catalase activity, and did not hydrolyze indoxyl acetate. The organisms were able to reduce nitrate and TTC, and were positive in the esterase, gamma-glutamyl transpeptidase, L-arginine arylamidase, and alkaline phosphatase tests, but negative in the hippurate hydrolysis, pyrrolidonyl arylamidase, and L-aspartate arylamidase tests. The bacteria grew well on blood-supplemented BHI, brucella and Mueller-Hinton agar media.

The bacteria were sensitive to all antimicrobials tested, as indicated by low MIC values, ranging from 0.03 to 0.25 µg/ml. They did not grow on media containing 1.5% NaCl, 1% bile or 1% glycine. They were able to grow at 37° C. and 30° C., but not at 25° and 42° C. Growth was abled in both anaerobic and microaerobic environments, while atmospheres containing normal levels of oxygen or solely an increase of $CO_2$ were not suitable to culture the bacteria.

The whole-cell protein profile of strain JKM4$^T$ (*Helicobacter cynogastricus*) differed considerably from those of reference strains of other *Helicobacter* species (FIG. 9A). Correlation levels towards the protein profiles of other *Helicobacter* reference strains were all below 0.80 indicating that strain JKM4$^T$ represents a novel *Helicobacter* species. FIG. 9B shows the result of the numerical analysis of the protein profiles of strain JKM4$^T$ (*Helicobacter cynogastricus*) and its nearest phylogenetic neighbours.

Genotypic Studies

Sequencing of the 16S rRNA gene of JKM4$^T$ (*Helicobacter cynogastricus*) revealed >97% homology with *H. felis*, *H. bizzozeronii*, *H. salomonis* and "Candidatus *H. heilmannii*", while the sequence differed more than 3% of "Candidatus *H. suis*" (FIG. 9B). A phylogenetic tree revealed clustering of the new isolate within all these species (FIG. 10).

PCR on genomic DNA of JKM4$^T$ (*Helicobacter cynogastricus*) using primers U430f (5'-gckgawttgatgcaagaagg-3') [SEQ ID NO:14 and U1735r (5'-cttcgtgrattttaarrccaat-3') [SEQ ID NO:15] produced a series of aspecific fragments and not the expected fragment of 1224 bp. PCR with "Candidatus *H. heilmannii*" specific primers Hh2f and Hh2r resulted in the production of a 320 bp fragment, which consistently differed from the expected 380 bp produced from DNA of "Candidatus *H. heilmannii*". Sequence analysis of the PCR product revealed a unique sequence, which did not match to any sequence in the Genbank.

Analysis of the PCR products produced from the DNA of the new isolate in the tDNA-PCR consistently revealed an amplicon of 136.6 bp, which differed from the tDNA-amplicon of *H. felis* (137 bp), *H. bizzozeronii* (136 bp) and *H. salomonis* (134 bp). A fragment of the same size was found in 1 cat (2.3%) and in 23 dogs (20.9%).

The present example demonstrates the existence of a fourth culturable *Helicobacter* species, able to colonize the canine stomach.

Analysis of the 16S rRNA gene revealed a high degree of homology with the three previously isolated carnivorous *Helicobacter* species.

The urease gene has recently been approved to be discriminative between these *Helicobacter* species. PCR on genomic DNA of isolate JKM4$^T$ (*Helicobacter cynogastricus*) using primers that detect the urease gene in *H. felis*, *H. bizzozeronii* and *H. salomonis* only produced aspecific fragments. A "Candidatus *H. heilmannii*" specific PCR did revealed a PCR fragment but with a sequence different to the one of Candidatus *H. heilmannii*".

In addition, the PCR amplicon of the novel species of the present invention by tDNA-PCR differs from the amplicons of other *Helicobacters*. These findings, together with the results of protein-profiling, which revealed a completely different pattern from the patterns of other *Helicobacter* species, demonstrate that isolate JKM4$^T$ is a distinct, novel *Helicobacter* species which we designate *Helicobacter cynogastricus*.

What is claimed is:

1. An isolated bacterium of the species *Helicobacter cynogastricus* deposited under Accession Number LMG P-23100.

2. A vaccine for immunization against Candidatus *Helicobacter suis* comprising a composition of one or more antigen preparations from *Helicobacter cynogastricus*.

3. The vaccine according to claim 2, wherein said antigen preparation comprises whole-killed bacteria.

4. The vaccine according to claim 2, wherein said antigen preparation comprises live-attenuated bacteria.

5. The vaccine according to claim 2, wherein said antigen preparation comprises a processed and/or artificial bacterial preparation.

6. The vaccine according to claim 2, wherein said antigen preparation comprises a bacterial lysate.

7. The vaccine according to claim 2, wherein said vaccine further comprises an adjuvant.

8. A method of vaccinating an animal against a Candidatus *Helicobacter suis* infection comprising administering to said animal a vaccine comprising one or more antigen preparations from one or more bacterial species, wherein said bacterial species is selected from the group consisting of *Helicobacter felis*, *Helicobacter pylori*, *Helicobacter cynogastricus* and *Helicobacter bizzozeronii*.

9. The method according to claim 8, wherein said antigen preparation comprises whole-killed bacteria.

10. The method according to claim 8, wherein said antigen preparation comprises live-attenuated bacteria.

11. The method according to claim 8, wherein said antigen preparation comprises a processed and/or artificial bacterial preparation.

12. The method according to claim 8, wherein said antigen preparation comprises a bacterial lysate.

13. The method according to claim 8, wherein said vaccine further comprises an adjuvant.

14. The method according to claim 8, wherein said vaccine is administered intranasally.

15. The method according to claim 8, wherein said vaccine is administered subcutaneously or intramuscularly.

16. The method according to claim 8, wherein said vaccine is administered prophylactically.

17. The method according to claim 8, wherein said vaccine is administered therapeutically.

18. The method according to claim 8, wherein said bacterial species is *Helicobacter felis*.

19. The method according to claim 8, wherein said bacterial species is *Helicobacter pylori*.

20. The method according to claim 8, wherein said bacterial species is *Helicobacter cynogastricus*.

21. The method according to claim 8, wherein said bacterial species is *Helicobacter bizzozeronii*.

* * * * *

UNITED STATES PATENT AND TRADEMARK OFFICE
CERTIFICATE OF CORRECTION

PATENT NO. : 7,780,951 B2  
APPLICATION NO. : 11/453170  
DATED : August 24, 2010  
INVENTOR(S) : Ducatelle et al.

Page 1 of 1

It is certified that error appears in the above-identified patent and that said Letters Patent is hereby corrected as shown below:

On the Title page, Item (56) under OTHER PUBLICATIONS, in Jalava, K., et al., replace "1-36-1038" with --1036-1038--;

Item (56) under OTHER PUBLICATIONS, in International Search Report (Mailed Feb. 13, 2007), replace "PCT/EP2008/005618" with --PCT/EP2006/005616--.

Column 7, Line 15, replace "by" with --bp--.

Column 11, Line 20, replace "(200)" with --(2000)--.

Column 13, Line 57, replace "bizzozeroni" with --bizzozeronii--.

Column 17, Line 17, replace "Immunisation" with --Immunization--.

Column 19, Lines 37-38, replace "(5'-TCA MC TAG GAC CGA GTC) [SEQ ID NO: 3]" with --(5'-TCA AAC TAG GAC CGA GTC) [SEQ ID NO: 3]--;

Lines 46-47, replace "(5'-MC TCA MG GM TTG ACG G-3') [SEQ ID NO: 9]" with --(5'-AAC TCA AAG GAA TTG ACG-3') [SEQ ID NO: 9]--.

Columns 27 and 28, under SEQ ID NO: 13, in <223> OTHER INFORMATION, replace "PCR primer Helicobacter urease" with --tRNA intergenic length polymorphism primer--.

Signed and Sealed this  
First Day of May, 2012

David J. Kappos  
*Director of the United States Patent and Trademark Office*